United States Patent [19]
Feng et al.

[11] Patent Number: 5,694,938
[45] Date of Patent: Dec. 9, 1997

[54] METHODOLOGY AND APPARATUS FOR DIFFUSE PHOTON MIMAGING

[75] Inventors: Shechao C. Feng; Fanan Zeng; Hui-Lin Zhao, all of Los Angeles, Calif.

[73] Assignee: The Regents of the University of California, Oakland, Calif.

[21] Appl. No.: 483,329

[22] Filed: Jun. 7, 1995

[51] Int. Cl.⁶ ..................................................... A61B 8/00
[52] U.S. Cl. ........................................ 128/664; 128/665
[58] Field of Search ................................. 128/664, 665, 128/653.1

[56] References Cited

U.S. PATENT DOCUMENTS

| | | |
|---|---|---|
| 5,137,355 | 8/1992 | Barbour . |
| 5,213,105 | 5/1993 | Gratton et al. ............... 128/664 |
| 5,258,825 | 11/1993 | Reed . |
| 5,309,907 | 5/1994 | Fang . |

OTHER PUBLICATIONS

M.A. O'Leary et al., "Images of Inhomogeneous Turbid Media Using Diffuse Photo Density Waves," OSA Proc on Advances in Optical Imaging & Photon Migration, vol. 21 (1994).

R.R. Alfano et al., "Time–Resolved Imaging of Translucent Droplets in Highly Scattering Turbid Media," Science, vol. 264:1913–15 (1994).

S.R. Arrige, "Iterative Reconstruction of Near Infrared Absorption Images," Inverse Probelsm in Scattering and Imaging, SPEI, vol 1767:372(1992).

H.L. Graber et al., "Near Infrared Absorption Imaging of Dense Scattering Media by Steady State Diffusion Tomography," Photon Migration in Imaging in Random Media and Tissues, SPIE, vol. 1888:372 (1993).

J.C. Schotland et al., "Photon Hitting Density" Applied Optics, vol 32, No. 4:448–53 (1993).

*Primary Examiner*—Marvin M. Lateef
*Assistant Examiner*—Derrick Fields
*Attorney, Agent, or Firm*—Daniel L. Dawes

[57] ABSTRACT

Non-invasive near infrared optical medical imaging devices for both hematoma detection in the brain and early tumor detection in the breast is achieved using image reconstruction which allows a mapping of the position dependent contrast diffusive propagation constants, which are related to the optical absorption coefficient and scattering coefficient in the tissue, at near infrared wavelengths. Spatial resolutions in the range of 5 mm for adult brain sizes and breast sizes can be achieved. The image reconstruction utilizes WKB approximation on most probable diffusion paths which has as lowest order approximation the straight line-of-sight between the plurality of sources and the plurality of detectors. The WKB approximation yields a set of linear equations in which the contrast optical absorption coefficients are the unknowns and for which signals can be generated to produce a pixel map of the contrast optical resolution of the scanned tissue.

24 Claims, 16 Drawing Sheets

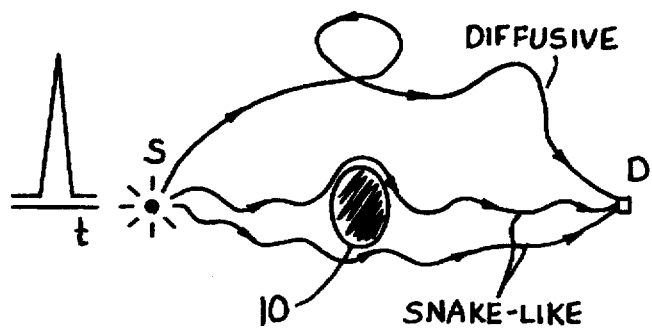
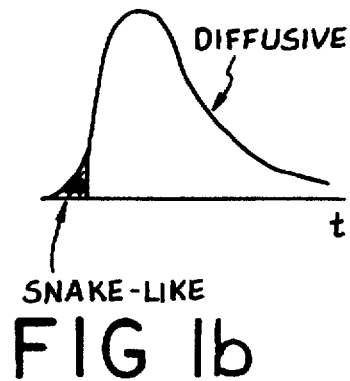
FIG 1a
FIG 1b
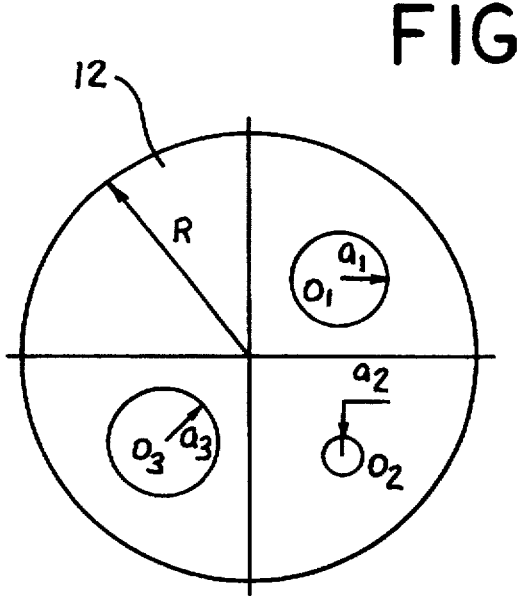
FIG 2

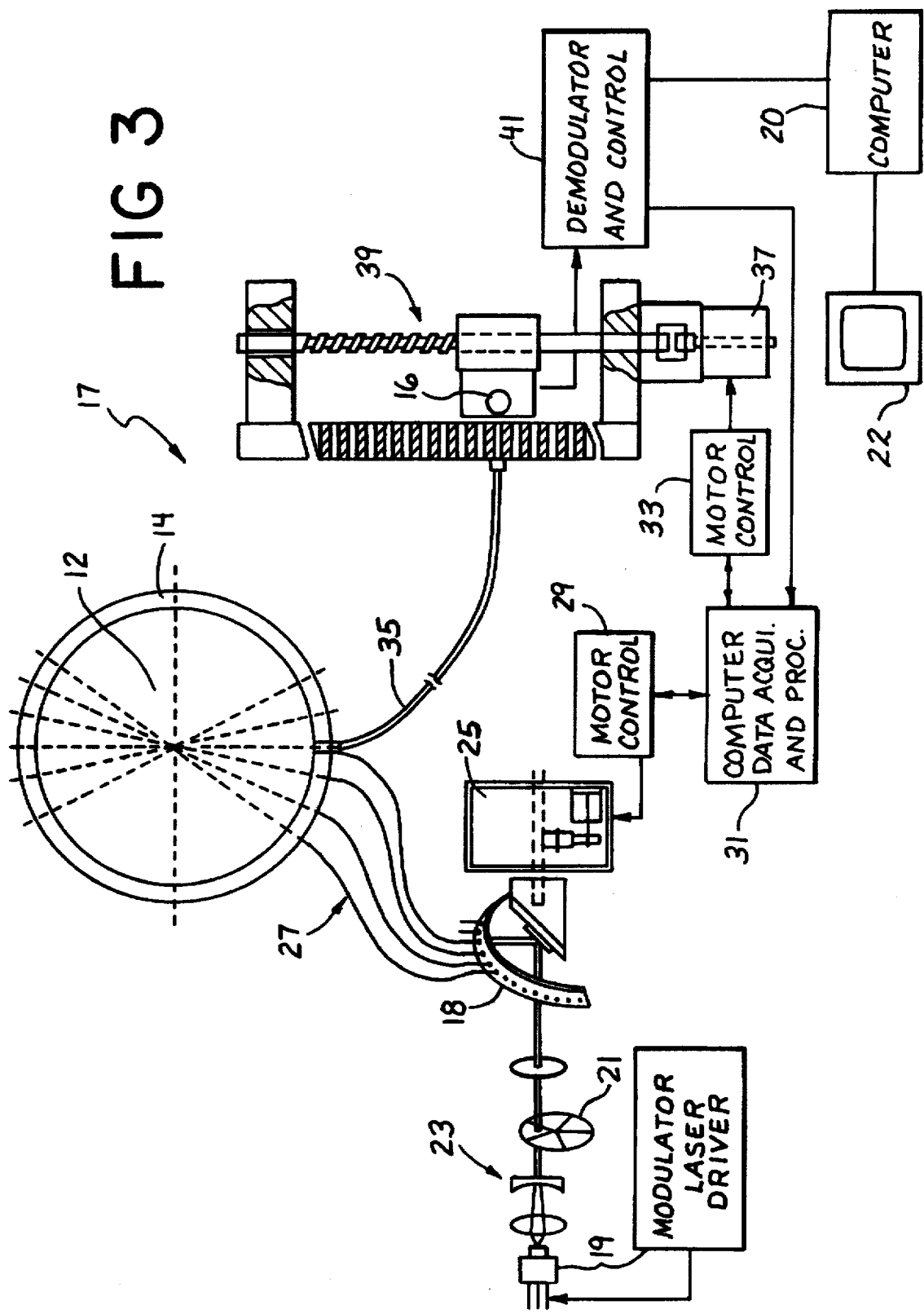

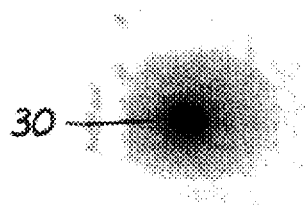
FIG. 4a
FIG. 4b
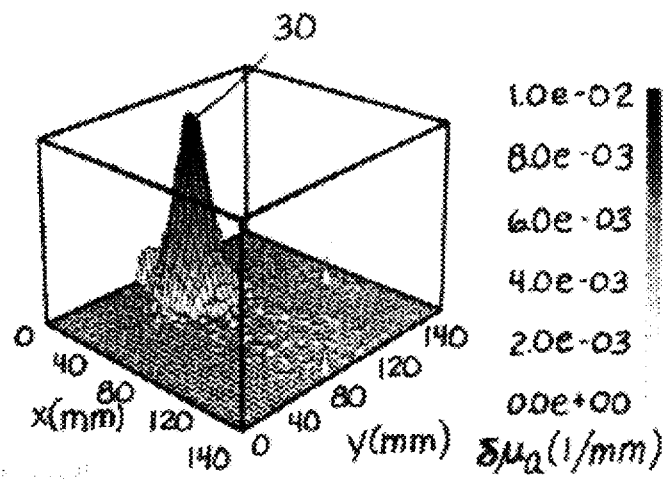
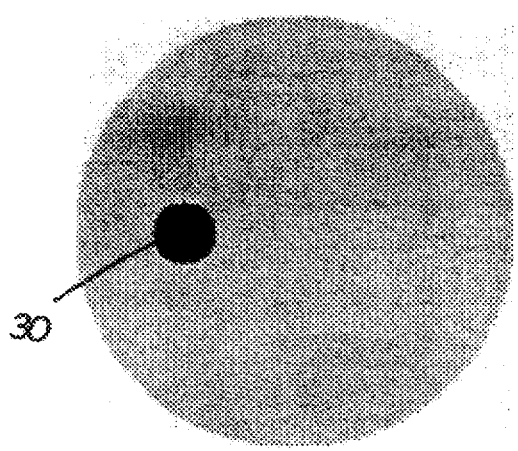
FIG. 4c
FIG. 4d
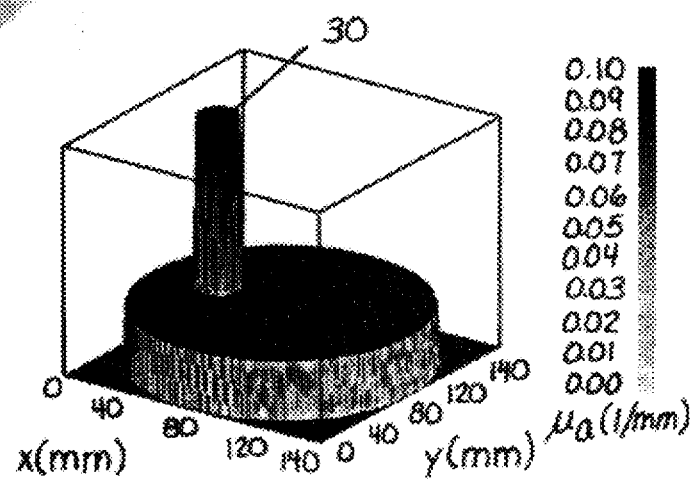

METHODOLOGY AND APPARATUS FOR DIFFUSE PHOTON MIMAGING

This invention was made in part with the assistance of government funding under the Office of Naval Research (ONR) Grant No. N00014-92-J-4004 from the Department of Defense, the Office of Basic Energy Research Grant No. DE-FG03-88ER45378 from the Department of Energy. The government may have rights to the invention.

BACKGROUND OF THE INVENTION

1. Field of the Invention

The invention relates to a method for performing computer tomography in media in which the photon migration process is diffusive.

2. Description of the Prior Art

Over the last two decades, the scope and important research being conducted in optical methods of medical diagnostics has increased dramatically. Much of the focus in this area has been in the use of near infrared light. Because near infrared light can penetrate relatively thick tissues, it can be used in many applications. One of the early successes using near infrared light was the determination of oxyhemagloben content in blood by the measurement of absorption coefficients at two or more wavelengths in the 700 to 900 nanometer range. This methodology is used as a diagnostic tool for tumors and hematomas in human tissue.

More recently, computer tomography (CT) based upon diffused near infrared photon migration through tissues has been investigated. See for example M. A. O'Leary et al., "Images of Inhomogeneous Turbid Media Using Diffuse Photo Density Waves," OSA Proceedings on Advances in Optical Imaging and Photon Migration, Vol. 21 (1994); R. R. Alfano et al., "Time-Resolved Imaging of Translucent Droplets in Highly Scattering Turbid Media," Science, Vol. 264:1913–15 (1994); S. R. Arridge, "Iterative Reconstruction of Near Infrared Absorption Images," Inverse Problems in Scattering and Imaging, SPIE, Vol. 1767:372 (1992); H. L. Graber et al., "Near Infrared Absorption Imaging of Dense Scattering Media by Steady State Diffusion Tomography," Photon Migration in Imaging in Random Media and Tissues, SPIE, Vol. 1888:372 (1993); and J. C. Schotland et al., "Photon Hitting Density," Applied Optics, Vol. 32, No. 4:448–53 (1993).

Compared with X-ray tomography, optical tomography has numerous advantages. Optical tomography is low cost to manufacture and operate, its near infrared light source is harmless to the human body, and the device is compact, sturdy and easily portable. However, there are intrinsic difficulties in obtaining images with high spatial resolution because of the diffuse nature of the light propagation in human tissue. Although near infrared light in the range of 700 to 900 nanometers is weakly absorbed in human tissue, the light is strongly scattered. The scattering is characterized by a transport scattering mean free path l*, which for typical tissue medium is about one millimeter and is characterized by a diffusive absorption length of about one centimeter.

The propagation of near infrared light in tissue can be described by the diffusion equation provided the length scale of interest is large compared to the transport scattering mean free path. Most theoretical studies on photon migration in human tissue is based on a form of the diffusion equation which assumes that the light source is isotropic, or on Monte Carlo simulations. The Monte Carlo method is a more general means of analysis for describing the photon migration process, but its application is limited in scope because it requires intensive, and in most cases, time consuming computations. In most situations of interest, where the system size is larger than the transport scattering mean free path, the diffusion equation for light provides a reasonably good description.

The key problem to be solved is the inverse problem of how to reconstruct the position, shape and size of an inhomogeneous region inside an otherwise homogeneous turbid medium from measurements made at the boundary of the medium. At present, most studies on this problem are executed using time resolved spectroscopy. The principle of time resolved spectroscopy is that the migrating photons detected by the detector can be qualitatively divided into two groups. Ballistic or snake photons in one group and diffusive photons in another is illustrated in the schematic paths shown in FIG. 1(a). The ballistic photons 11 are those that travel short distances and the diffusive photons 13 are those that travel long distances. If the light source emits a short pulse, typically a few picoseconds in length, the detector has a time gate which only records the ballistic or snake photons 11 which is shown in the shaded portion of the graph of FIG. 1(b). A relatively sharp image of an inhomogeneous region 10, such as a tumor or hematoma embedded inside tissue 15, can thus be obtained See for example R. R. Alfano, supra.

The drawback of time resolved spectroscopy is two-fold. First, it requires a short pulse-like source and short time-gated detectors, both of which are expensive. Second, a signal at the detectors contains only an exponentially small fraction ($\sim e^{-L/l^*}$) of the total number of photons emitted by the source. Therefore, the signal-to-noise ratio is intrinsically low and extremely sensitive and, therefore, expensive detectors are required. Due to this reason, time resolved spectroscopy can be applied and practiced only for tissue samples with a thickness no greater than about five centimeters.

An alternative is to use continuous wave (CW) sources and detect photons arriving at all times. In a continuous wave approach, the intensity of the detectors will be high, but the diffusive photons contained in the signal will severely blur the image. Therefore, some way must be found to extract useful information from this diffuse signal. The continuous wavelength source is usually frequency modulated so that the photon density has an AC component which is selectively detected.

The current method for image reconstruction in the frequency domain is based on the first order perturbation of photon fluence rate due to variations of the position dependent absorption coefficient plus iteration. This corresponds to summing up the single scattering events of the small variations of the absorption coefficient. The drawback of the frequency domain approach is that it requires the variations in the absorption coefficient to be small, which in most realistic in vivo systems is not the case, such as a hematoma 10 within human brain tissue 15 (see FIG. 1(a)).

Therefore, what is needed is some type of imaging methodology which is not limited by the shortcomings of prior art approaches, but can be used in general in any in vivo system and still obtain a high resolution image using lower cost detectors.

BRIEF DESCRIPTION OF THE INVENTION

The invention is a method for optical tomography of a target disposed in space. The method comprises the steps of exposing a target with an amplitude modulated optical signal at a given modulation frequency $f = \omega/2\pi$ generated by a source at a source position next to the target. The amplitude modulated (frequency domain) optical signal from the source is detected at a detection position next to the target. If optical signal is gathered in the time domain using a pulsed source, a Fourier transform at frequency f gives the same frequency domain optical signal. A line of most probable diffusion path is defined between the source and detection positions, which to first order is simply the straight line of sight between the source and the detector. (The precise definition of most probable diffusion path will be given below, in Equation (21).) A pixel lattice is defined in a computer corresponding to the space in which the target is located. The pixel lattice is comprised of a plurality of pixel cells. A plurality of contrast diffusive propagation constants, $\delta\kappa(x_i)=\kappa(x_i)-\kappa_0$, are defined for each of the pixel cells. $\kappa_0$ is the propagation constant in a reference homogeneous medium, which may be chosen as one with the expected average optical properties of the target. $\kappa(x_i)$ is related to the optical absorption coefficient $\mu_a(x_i)$ and the transport (or reduced) scattering coefficient $\mu'_s(x_i)$ of the target at the spatial position corresponding to each of the selected pixel cells within the pixel lattice. (The precise relation will be given below, in Equation (14).) The most probable diffusion path between the source and detection position is disposed across the plurality of pixel cells to select a subplurality of the pixel cell of the lattice. An equation then relates the corresponding subplurality of contrast diffusive propagation constants $\delta\kappa(x_i)$ to the photon flux for the reference homogeneous medium $J_O$ and measured photon flux $J_M$ at the detection position b given a source position a by Equation (1) below.

$$\sum_i \delta\kappa(x_i)\Delta l_i = \ln[J_O(b,a,\omega)/J_M(b,a,\omega)], \tag{1}$$

where the sum is over the subplurality of pixel cells traversed by the most probable diffusion path, $\Delta l_i$ is the length of the line segment of the most probable diffusion path within each pixel cell. Performing this procedure for a large combination of different source and detection positions, such that all pixel cells in the target are reached by the most probable diffusion paths for some source and detection position, an optical tomograph of the target represented in the lattice may be provided.

Optical tomography with diffuse photons using Equation (1) as the signal processing method is defined for the purposes of this specification as a "WKB image reconstruction".

The method further comprises generating a graphic image from the plurality of imaging variables. This entails solving for the contrast diffusive propagation constants $\delta\kappa(x_i)$ in each pixel cell using Equation (1), for detected signals $J_M$ corresponding to source positions and detection positions taken at a plurality of pairs of positions next to the target.

The plurality of source and detection positions may lie in a plane so that a two-dimensional graphic image is generated, or the plurality of the source and detection positions may be disposed on a three-dimensional surface which includes the target so that a three-dimensional graphic image is generated.

In one embodiment the plurality of contrast diffusive propagation constants $\delta\kappa(x)$ is generated by means of single value decomposition of a plurality of linear equations (1) governing the contrast diffusive propagation constants. In another embodiment the plurality of contrast diffusive propagation constants is generated by means of simultaneous algebraic reconstruction of the contrast diffusive propagation constants. In still a third embodiment the plurality of contrast diffusive propagation constant is generated by means of filtered back projection of the contrast diffusive propagation constants. This third method may be used only with the first order approximation for the most probable diffusion path which corresponds to straight lines of sight between each source and detector position.

In the illustrated embodiment the optical signal is an amplitude modulated near infrared signal. The wavelength of the near infrared signal is in the range of 700 to 900 nanometers. These parameters are chosen to correspond to best optical penetration of human tissue.

In yet another embodiment the method further comprises the step of exposing the target to the light source at a plurality of amplitude modulated frequencies in sequence. The optical signals detected at the plurality of detection positions for the plurality of modulation frequencies are used simultaneously for solving for the contrast diffusive propagation constants in each pixel cell and generating the resulting image. This embodiment is suited for time-domain optical measurement using a pulsed source and the detection of time resolved optical signal. Fourier transform of the resulting time-domain optical signal generates the multiple frequency inputs needed for this embodiment.

The method includes the operation wherein the target is exposed to a plurality of light sources in sequence. The plurality of light sources is positioned at a plurality of distinct source positions so that the time sequence identifies which of the plurality of light sources is activated.

The invention is alternatively defined as a method of producing a near infrared mograph of a tissue mass comprising the steps of irradiating the tissue mass with an amplitude modulated light from a near infrared light source. The AM modulated near infrared light is detected at a plurality of detection positions. A line of most probable diffusion path, which to first order is the straight line of sight, is defined between the near infrared light source and each of the detection positions. An optical image of the tissue mass is reconstructed from the detected AM modulated near infrared light signals using WKB image reconstruction. As a result, stable and high resolution near infrared tomography is provided.

The method further comprises the step of irradiating the tissue mass with amplitude modulated near infrared light from a plurality of near infrared light sources. Each of the sources defines a line of most probable diffusion path for WKB image reconstruction with each of the plurality of near infrared detectors at each of the detection positions. The method still further comprises irradiating the tissue mass with AM modulated near infrared light from the light source at a plurality of modulated frequencies, which may be obtained equivalently using a time-domain measurement using pulsed sources with a subsequent Fourier transformation.

The invention may now be better visualized by turning to the following Figures wherein like elements are referenced by like numerals.

BRIEF DESCRIPTION OF THE DRAWINGS

FIG. 1(a) is a diagram illustrating the path of quasi ballistic (snake) photons and diffuse photons through a relatively homogeneous tissue mass, such as the brain or breast, containing an inhomogeneous body, such as a hematoma or tumor.

FIG. 1(b) is a simplified graph illustrating the typical time resolved spectrum for quasi ballistic and diffuse photons in tissue.

FIG. 2 is a diagram showing an approximate cylindrical model tissue mass with three off-center foreign or inhomogeneous bodies placed in the plane of a detector and source array from which a near infrared tomograph is made.

FIG. 3 gives the block diagram of a proposed hardware system for performing near infrared tomography using the WKB image reconstruction method in this invention. To save cost, the proposed prototype uses a single source and a single detector together with a time-sharing optical coupling system using optical fibers and fiber bundles. Later it can be generalized to include multiple sources and multiple detectors.

FIG. 4(a) is a reconstructed cross-sectional image, in gray scale, simulating the human brain using the method of the invention of an infinite tissue medium having a single off-center spherical model hematoma using computed data corresponding to an exact solution of the diffusion equation. The imaginary circle, on which 128 sources and 64 detectors are located, has a radius R=70 mm. The spherical inclusion has a radius a=10 mm and is located at (−35 mm, 0 mm). The modulation frequency used is f=200 MHz. The optical parameters used are: $\mu_{ao}$=0.003 mm$^{-1}$ for the surrounding medium, $\mu_{a1}$=0.1 mm$^{-1}$ for the model hematoma sphere, and $\mu'_{so}$=$\mu'_{a1}$=1.6 mm$^{-1}$ for both media. The upper left figure is the reconstructed image in gray scale. FIG. 4(b) is a three-dimensional graph of FIG. 4(a) where the x and y axes are spatial coordinates, and the z axis is the reconstructed contrast absorption coefficient signal. FIG. 4(c) is the input absorption coeficient map in gray scale, and FIG. 4(d) is the corresponding three-dimensional graph.

Figure 5A:
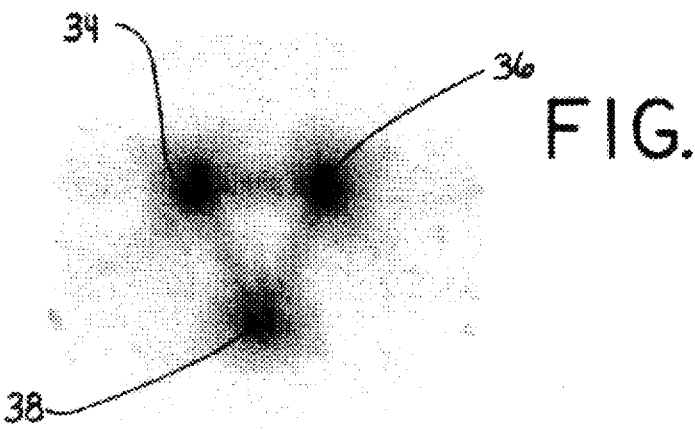
FIG. 5(a) is a reconstructed cross-sectional image, in gray scale, simulating the human brain using the method of the invention of a model cylindrical tissue mass having three off-center cylindrical model hematomas using computed photon diffusion data. The modulation frequency used is f=200 MHz. The radius of the model tissue mass is R=70 mm. The radii of the three inclusions are $a_1$=$a_2$=$a_3$=10 mm and their center locations are $O_1$=(−20 mm, 20 mm), $O_2$=(20 mm, 20 mm ) and $O_3$=(0, 20 mm). The optical parameters are $\mu_{ao}$=0.003 mm$^{-1}$ for the tissue medium, $\mu_{a1}$=0.1 mm$^{-1}$ for the model hematoma, and $\mu'_{so}$=$\mu'_{s1}$=1.6 mm$^{-1}$ for both media. The FIG. 5(a) is the reconstructed image in gray scale.
Figure 5B:
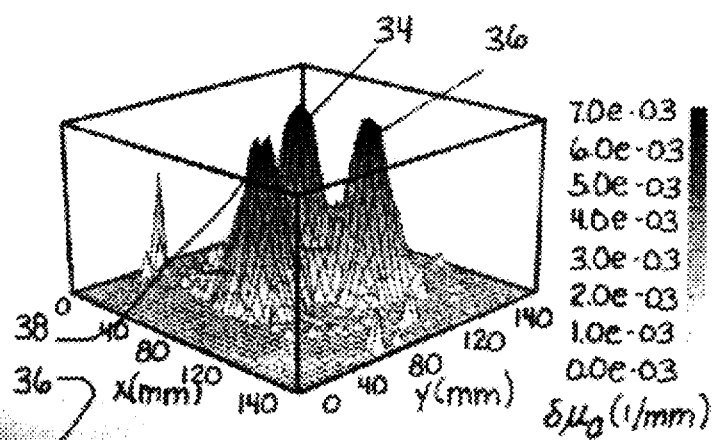
FIG. 5(b) is a three-dimensional graph of FIG. 5(a) where the x and y axes are spatial coordinates, and the z axis is the reconstructed contrast absorption coefficient signal.
Figure 5C:
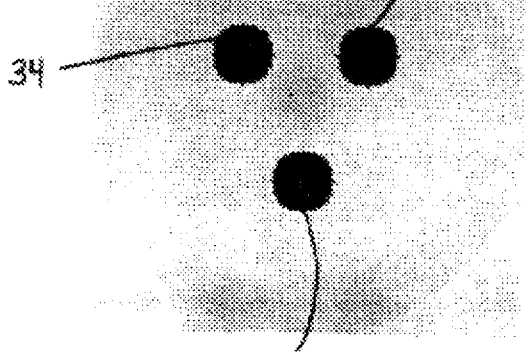
FIG. 5(c) is the input absorption coeficient map in gray scale.
Figure 5D:
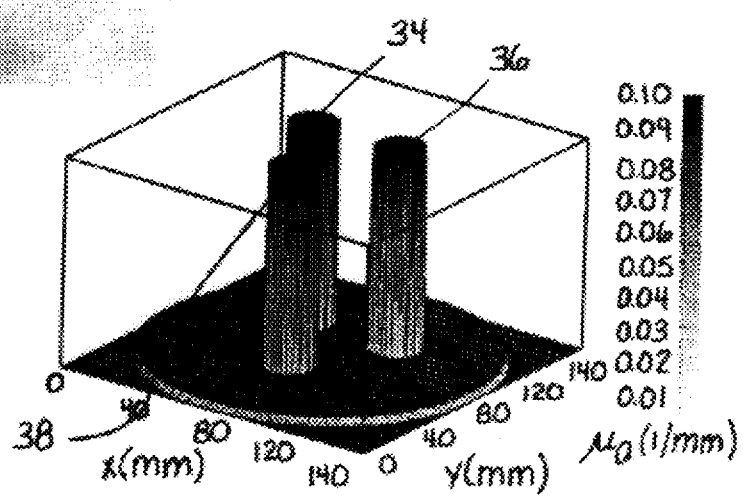
FIG. 5(d) is the corresponding three-dimensional graph.
Figure 6A:
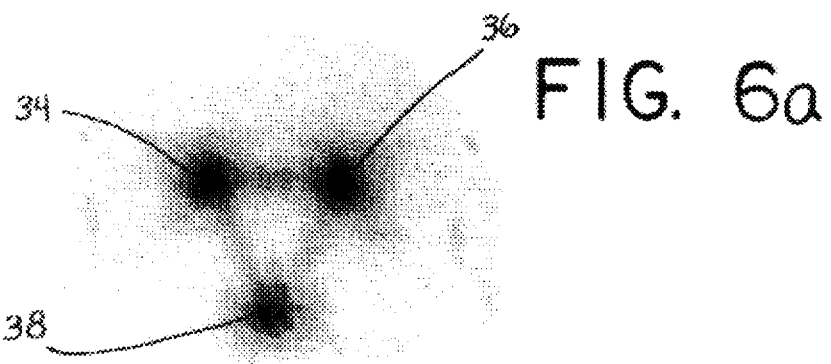
FIG. 6(a) is the reconstructed cross-sectional image of FIG. 5 in which 10% Gaussian noise has been added to the data.
Figure 6B:
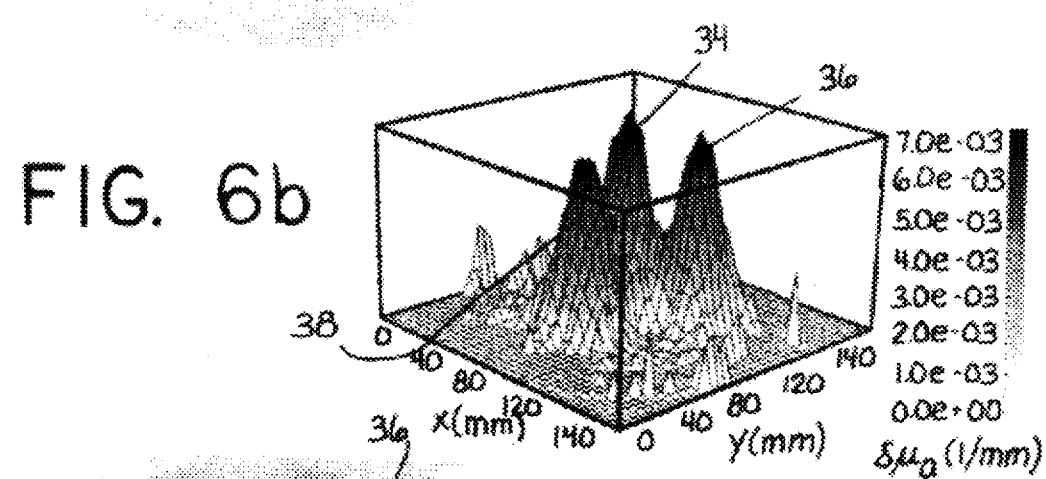
FIG. 6(b) is a three-dimensional graph of FIG. 6(a) where the x and y axes are spatial coordinates, and the z axis is the reconstructed contrast absorption coefficient signal.
Figure 6C:
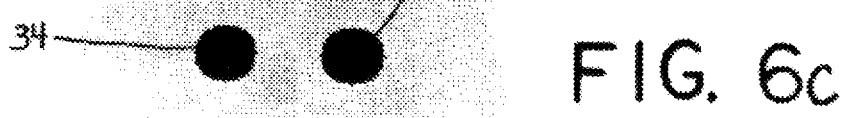
FIG. 6(c) is the input absorption coeficient map in gray scale.
Figure 6D:
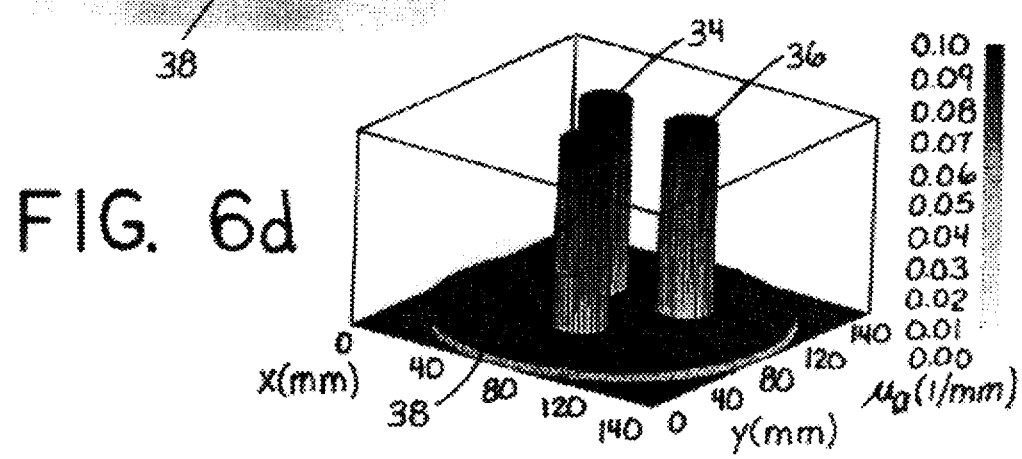
FIG. 6(d) is the corresponding three-dimensional graph.
Figure 7A:
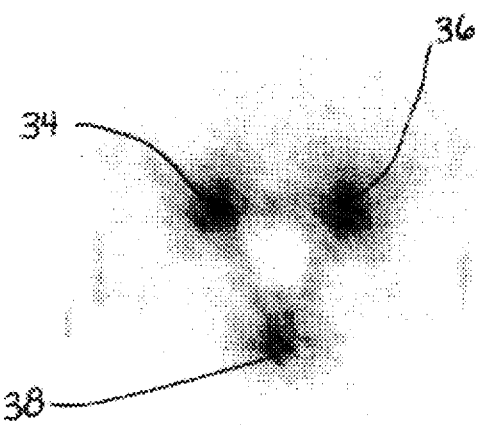
FIG. 7(a) is the reconstructed cross-sectional image of FIG. 5 in which 20% Gaussian noise has been added to the data.
Figure 7B:
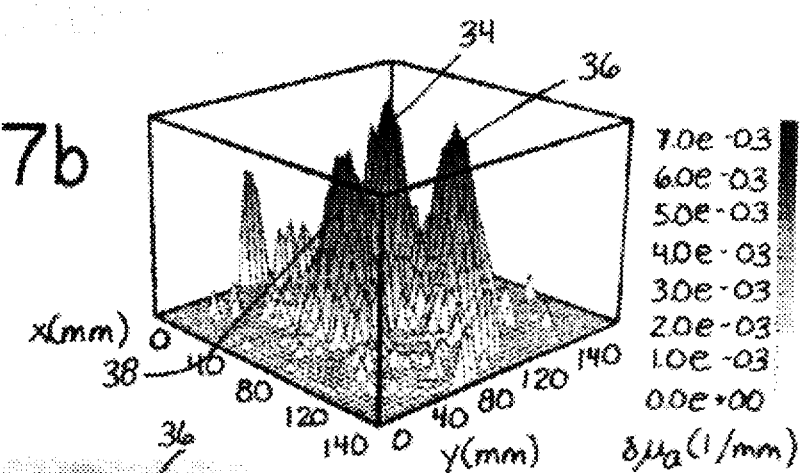
FIG. 7(b) is a three-dimensional graph of FIG. 7(a) where the x and y axes are spatial coordinates, and the z axis is the reconstructed contrast absorption coefficient signal.
Figure 7C:
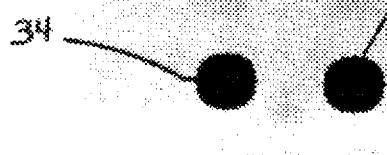
FIG. 7(c) is the input absorption coeficient map in gray scale.
Figure 7D:
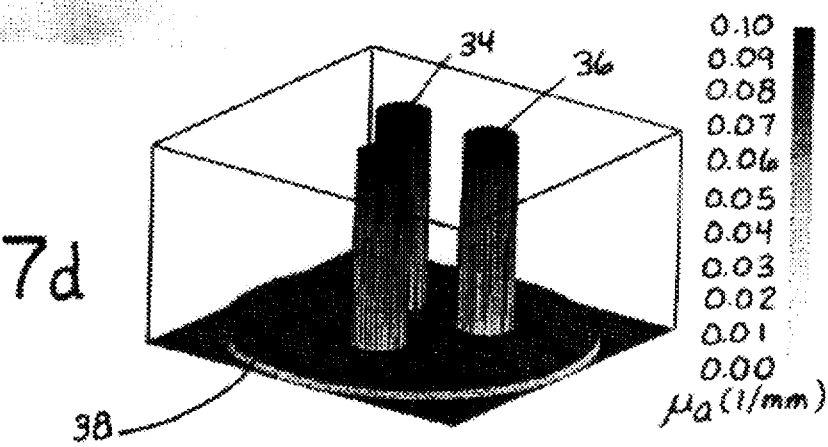
FIG. 7(d) is the corresponding three-dimensional graph.
Figure 8A:
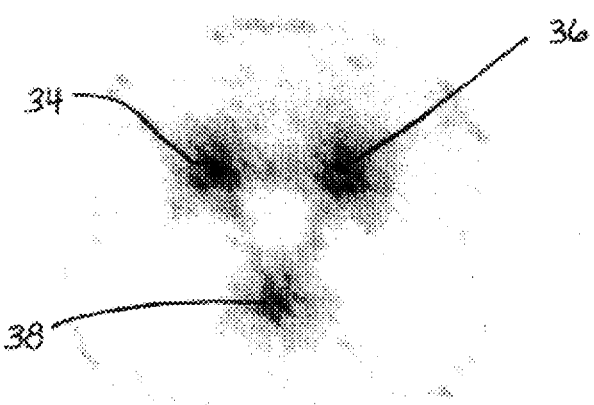
FIG. 8(a) is the reconstructed cross-sectional image of FIG. 5 in which 30% Gaussian noise has been added to the data.
Figure 8B:
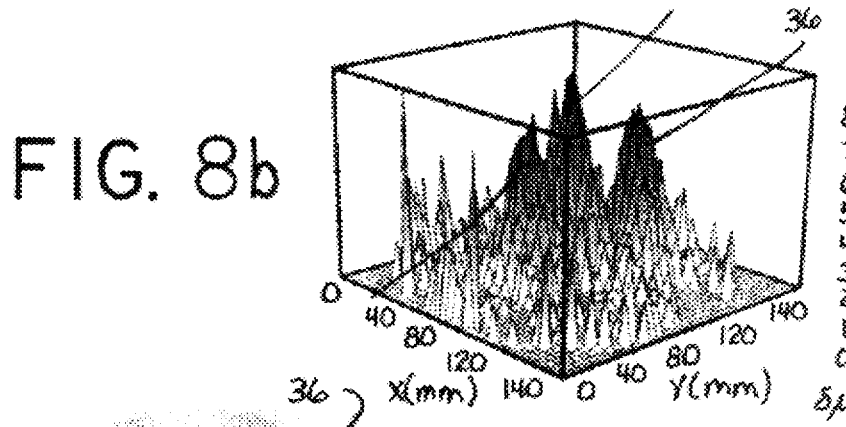
FIG. 8(b) is a three-dimensional graph of FIG. 8(a) where the x and y axes are spatial coordinates, and the z axis is the reconstructed contrast absorption coefficient signal.
Figure 8C:
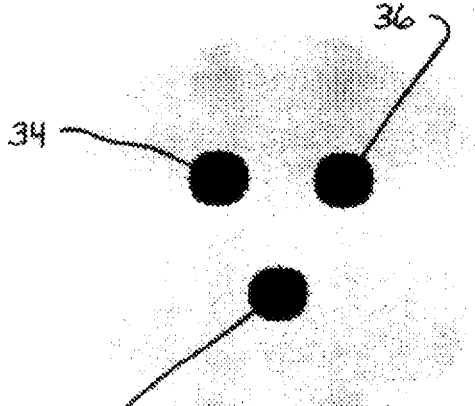
FIG. 8(c) is the input absorption coeficient map in gray scale.
Figure 8D:
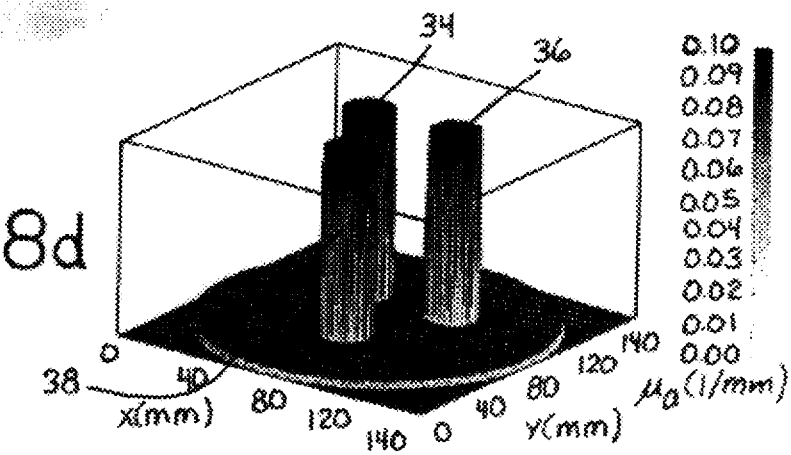
FIG. 8(d) is the corresponding three-dimensional graph.
Figure 9A:
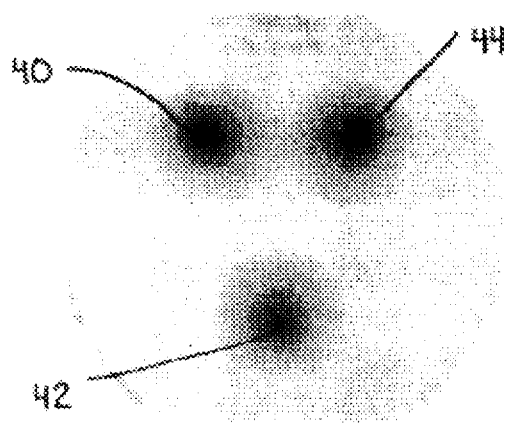
FIG. 9(a) is a reconstructed cross-sectional image simulating the human breast using the method of the invention of a cylindrical tissue mass having three off-center cylindrical model tumors using computed photon diffusion data. The modulation frequency used is f=200 MHz. The radius of the model tissue mass is R=50 mm. The three inclusions are: $a_1$=5 mm at (−15 mm, 20 mm), $a_2$=5 mm at (15 mm, 20 mm) and $a_3$=5 mm at (0 mm, −20 mm). The optical parameters are $\mu_{ao}$=0.008 mm$^{-1}$, $\mu_{a1}$=0.024 mm$^{-1}$, and $\mu'_{so}$=$\mu'_{s1}$=1 mm$^{-1}$.
Figure 9B:
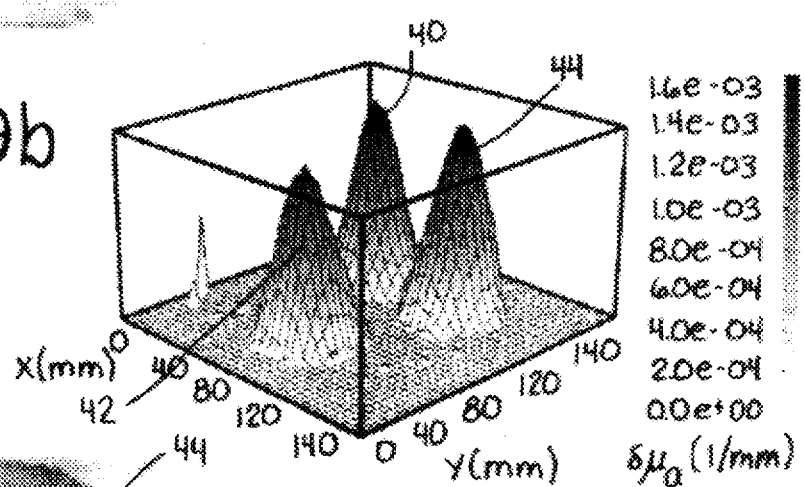
FIG. 9(b) is a three-dimensional graph of FIG. 9(a) where the x and y axes are spatial coordinates, and the z axis is the reconstructed contrast absorption coefficient signal.
Figure 9C:
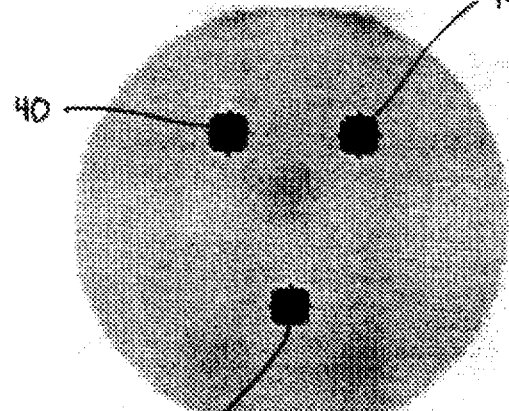
FIG. 9(c) is the input absorption coeficient map in gray scale.
Figure 9D:
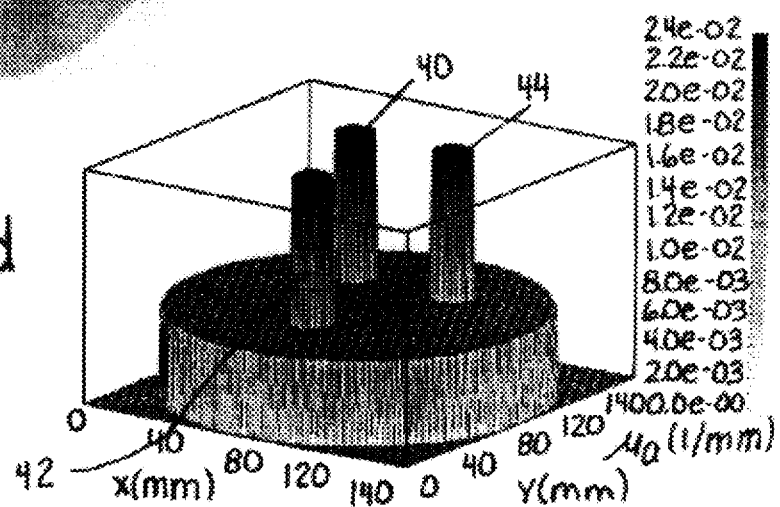
FIG. 9(d) is the corresponding three-dimensional graph.
Figure 10A:
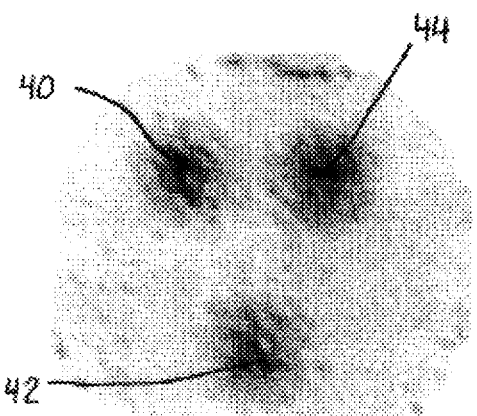
FIGS. 10(a)–(d) and 11(a)–(d) are images reconstructed using the same data as in FIG. 9(a)–(d) except that Gaussian random noises are added to the data. The two images correspond, respectively, 5% and 10% noise levels respectively. It is observed that for smaller inclusions (compared to those in FIG. 5(a)–8(a)) and for lower level of contrast in the absorption coefficient between the inclusion and the surrounding tissue, noise has a larger effect on the image quality here.
Figure 10B:
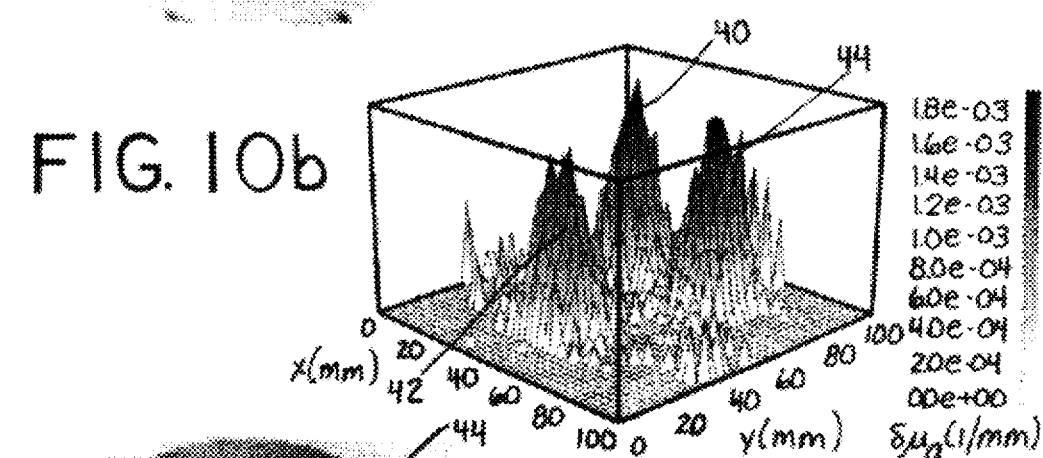
Figure 10C:
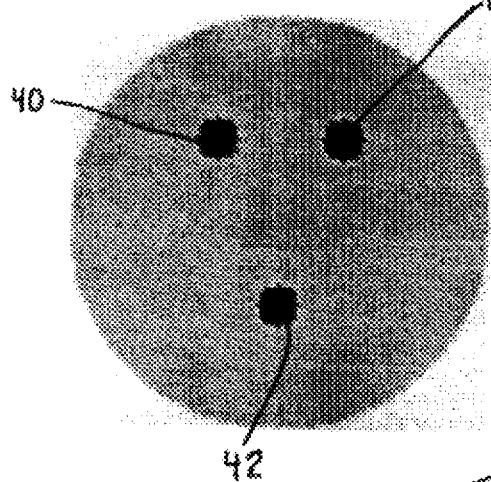
Figure 10D:
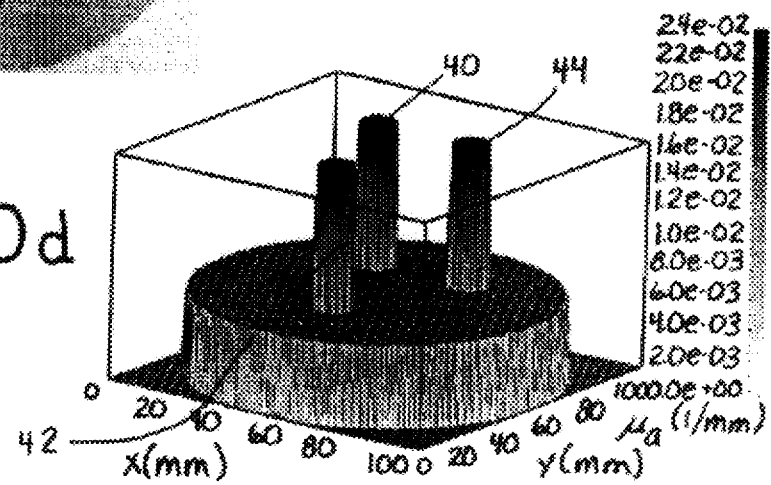
Figure 11A:
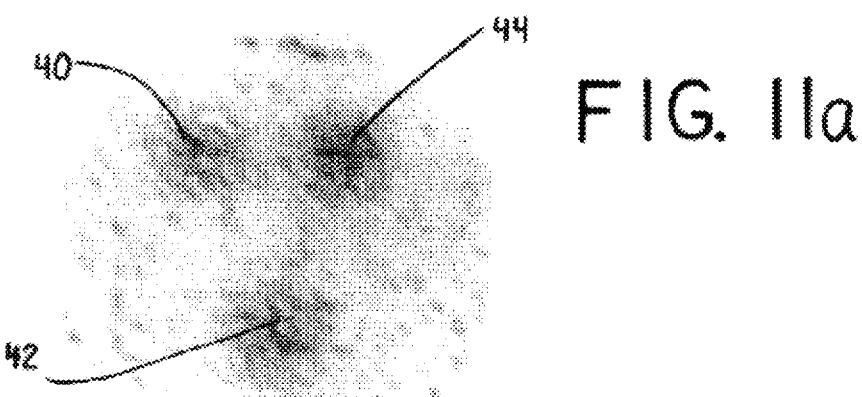
Figure 11B:
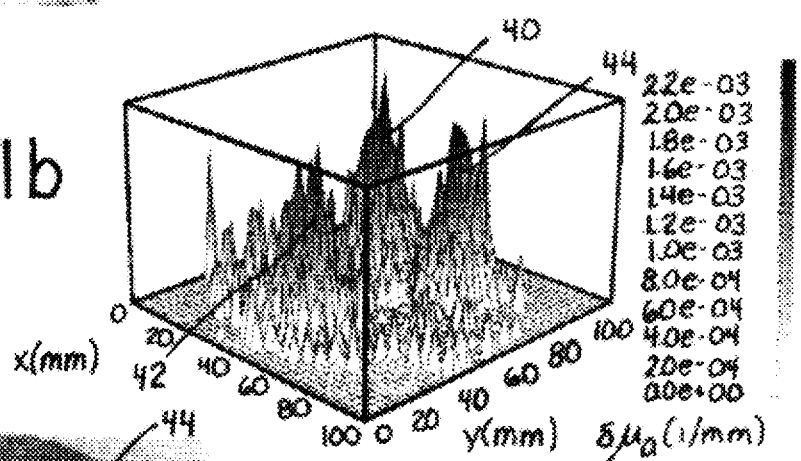
Figure 11C:
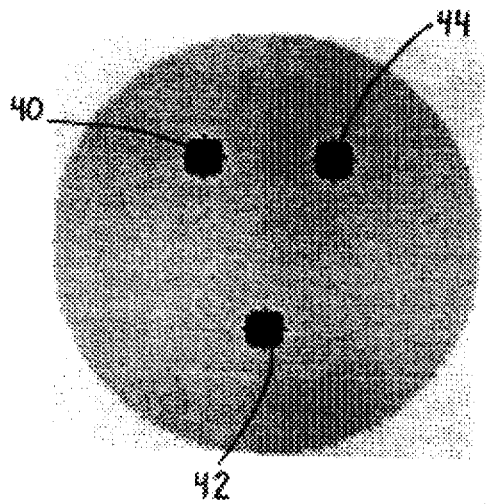
Figure 11D:
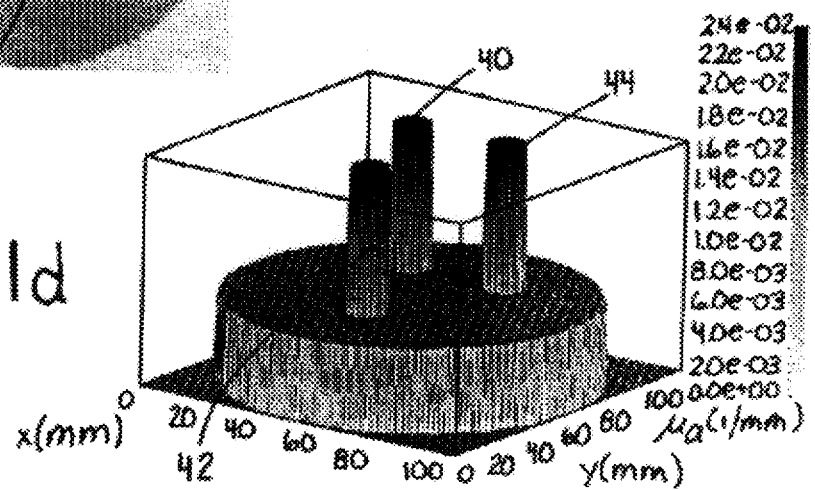
Figure 12A:
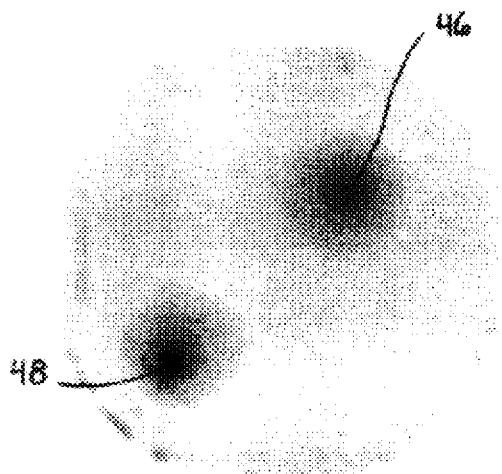
FIG. 12(a)–(d) is a reconstructed cross-sectional image simulating the human breast using the method of the invention of a cylindrical tissue mass having two off-center cylindrical tumors using computed diffusion data.
Figure 12B:
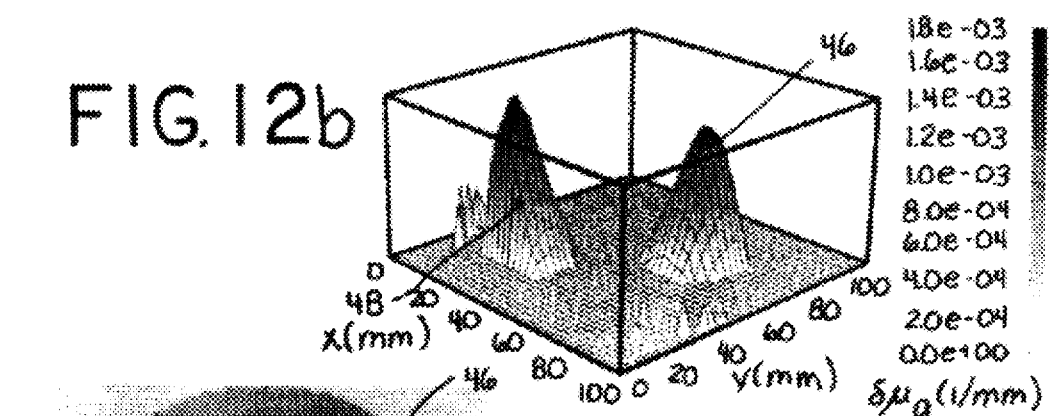
Figure 12C:
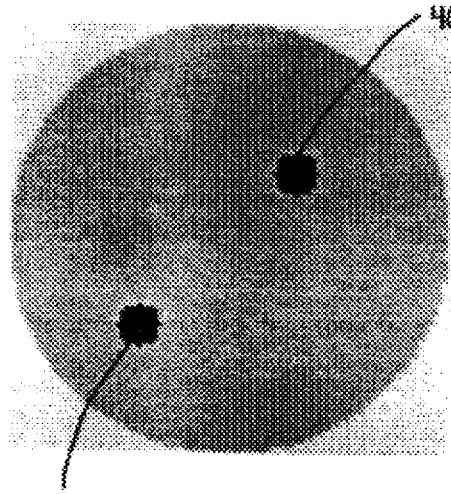
Figure 12D:
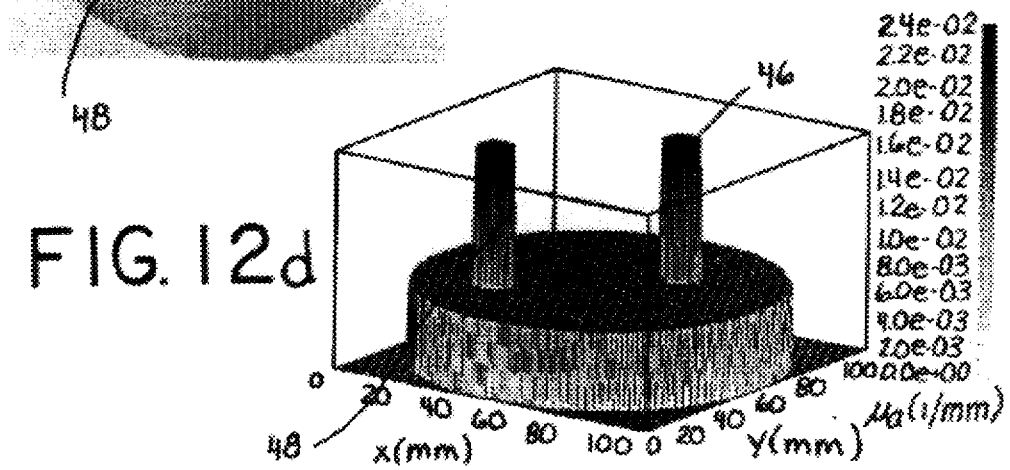
Figure 13A:
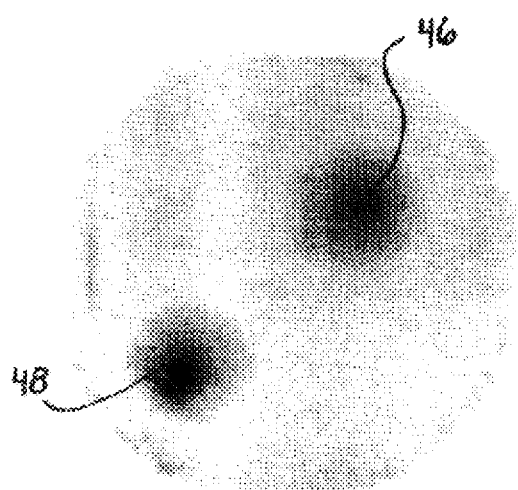
FIG. 13(a)–(d) is the reconstructed cross-sectional image of FIG. 12(a)–(d) in which a spatial Gaussian distribution of 3% in the fluctuation amplitude of the optical absorption coeftldent of the background tissue mass has been added in generating the forward data.
Figure 13B:
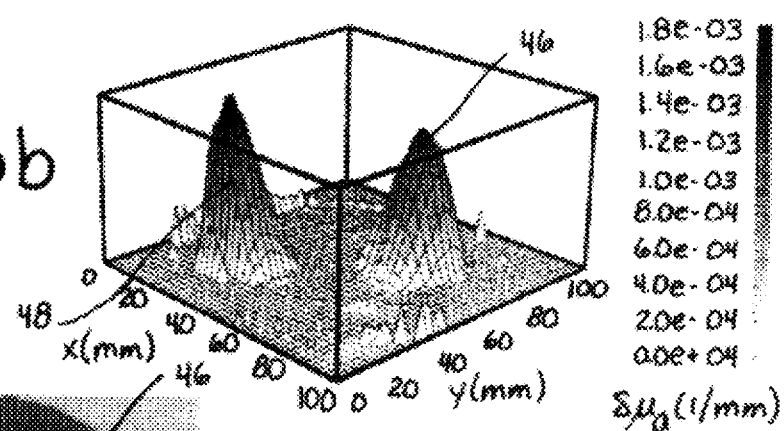
Figure 13C:
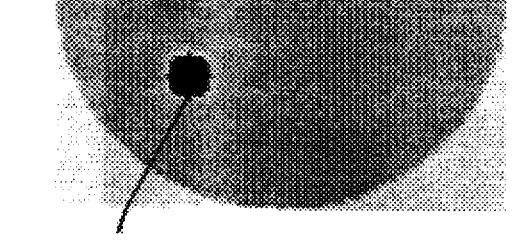
Figure 13D:
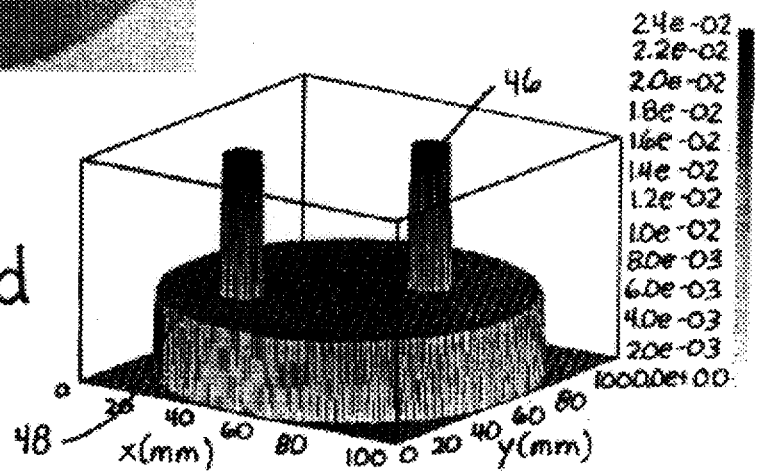
Figure 14A:
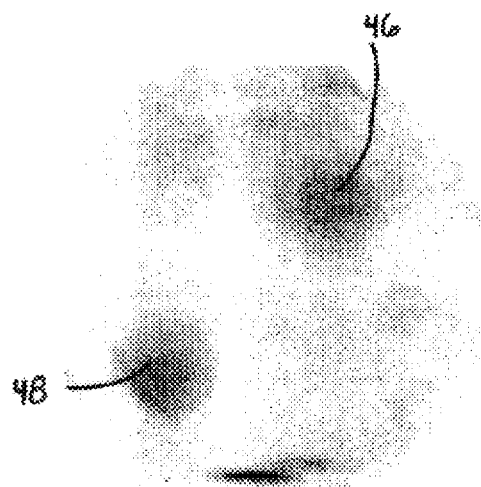
FIG. 14(a)–(d) is the reconstructed cross-sectional image of FIG. 12(a)–(d) in which a spatial Gaussian distribution of 15% in the fluctuation amplitude of the optical absorption coefficient of the background tissue mass has been added in generating the forward data.
Figure 14B:
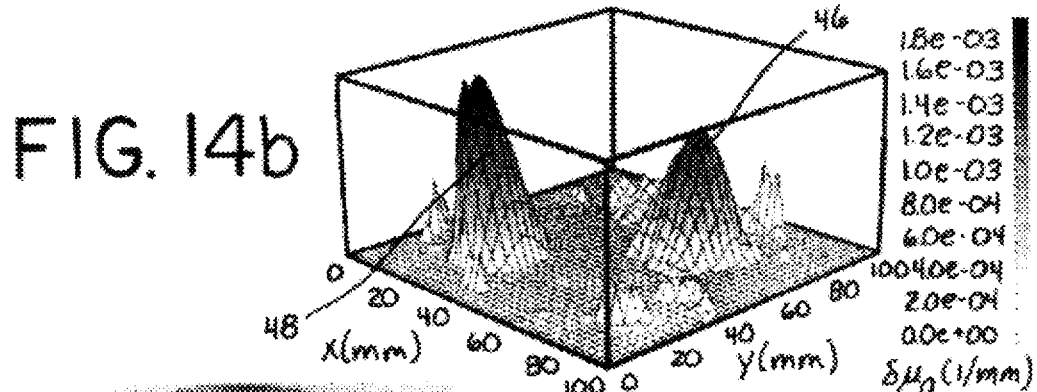
Figure 14C:
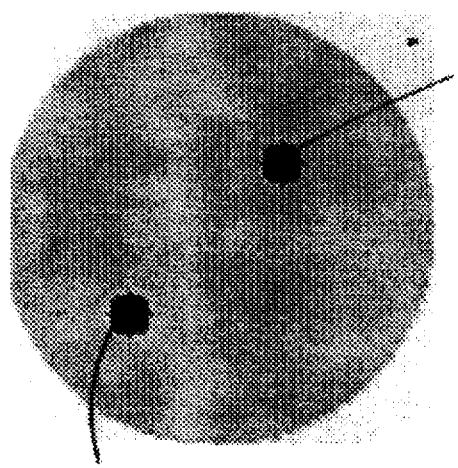
Figure 14D:
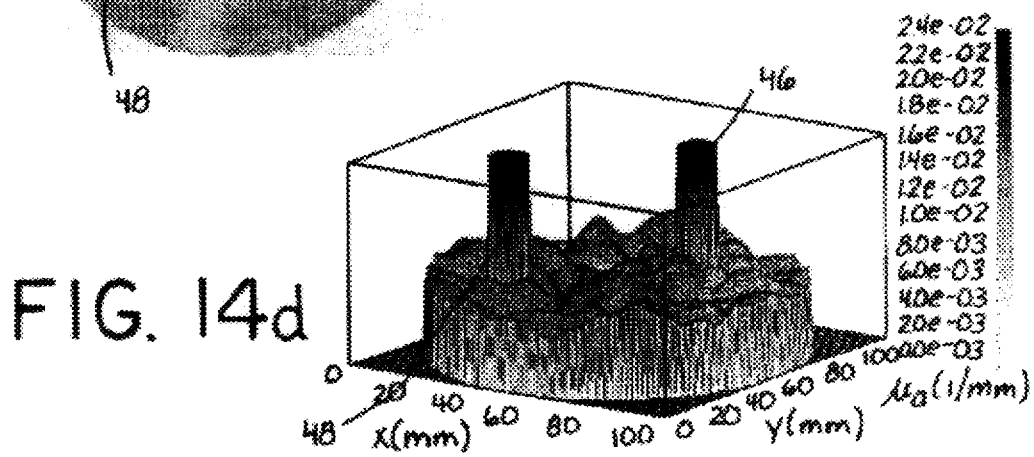
Figure 15A:
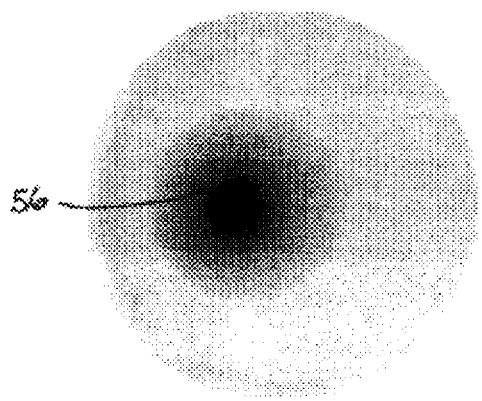
FIG. 15(a) is the reconstructed cross-sectional image, in gray scale, of the contrast diffusive propagation constant δκ(x), using Equation (1), from computer generated mock data. The geometry is an infinite tissue medium containing a single spherical hematoma with a=10 mm at (15 mm, 0. mm). Sources and detectors are placed on an imaginary circle with radius R=70 mm. The optical parameters used are $\mu_{ao}$=0.003/mm, $\mu_{a1}$=0.10/mm, $\mu_{so}$=µs1=1.6 /mm. The SART method is used for the real part of the δκ(x) only. The modulation frequency f=200 MHz is used. The pixel lattice of 128×128 is used. No noise is included.
Figure 15B:
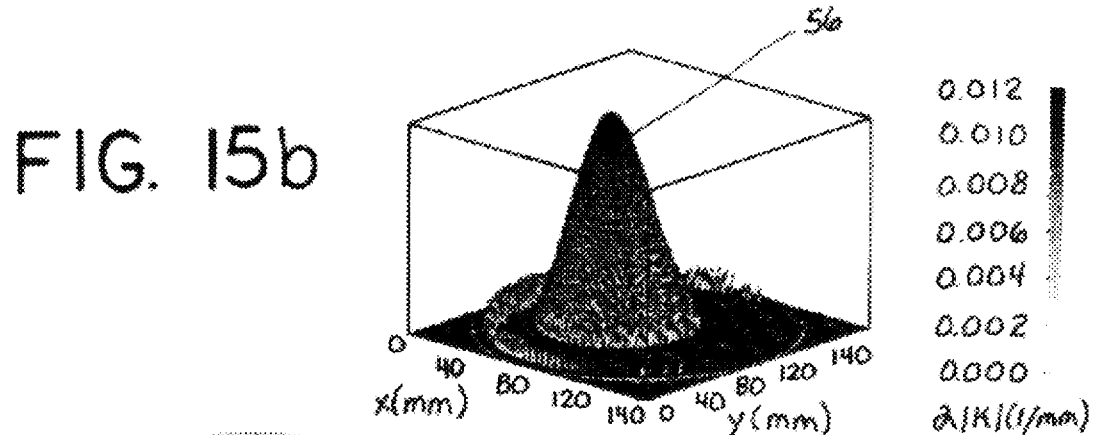
FIG. 15(b) is a three-dimensional graph of FIG. 15(a) where the z and y axes are spatial coordinates, and the z axis is the reconstructed contrast diffusive propagation constant signal.
Figure 15C:
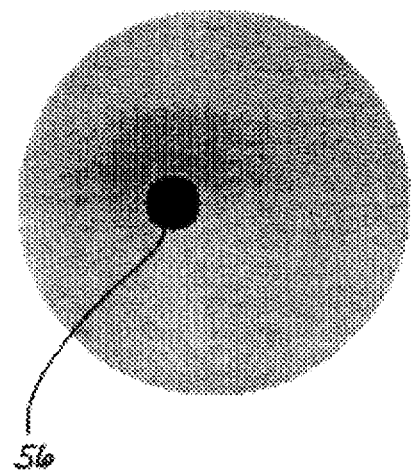
FIG. 15(c) is the input diffusive propagation constant coeficient map in gray scale.
Figure 15D:
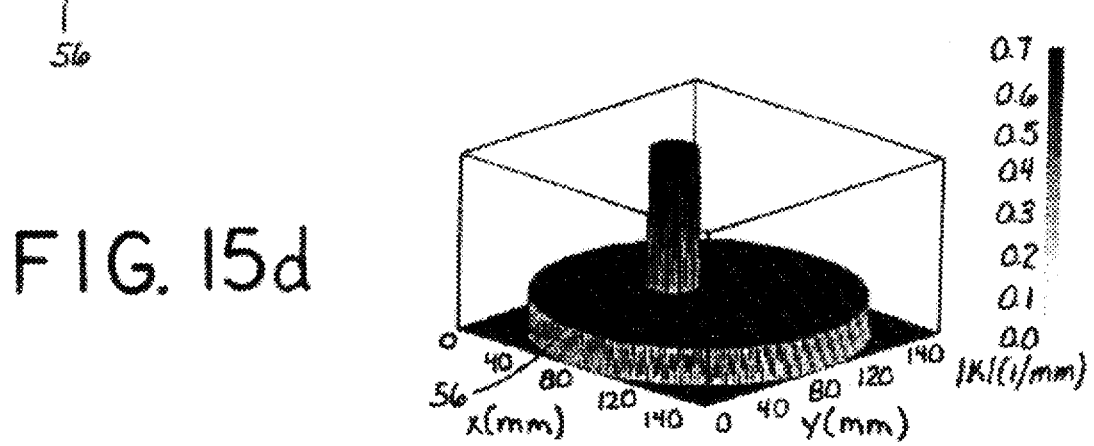
FIG. 15(d) is the corresponding three-dimensional graph.
Figure 16A:
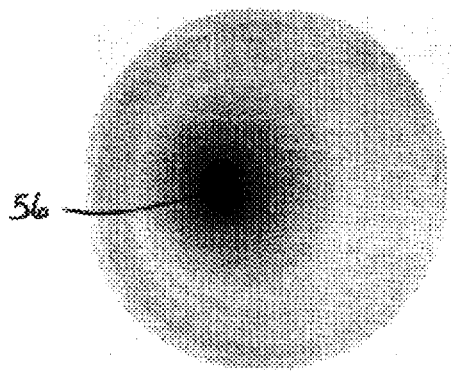
FIGS. 16(a)–(d) are the reconstructed cross-sectional images of FIG. 15 respectively except both real and imaginary parts of δκ(x) are used here for image reconstruction, which is equivalent to using both the amplitude and the phase of the amplitude modulated optical signal.
Figure 16B:
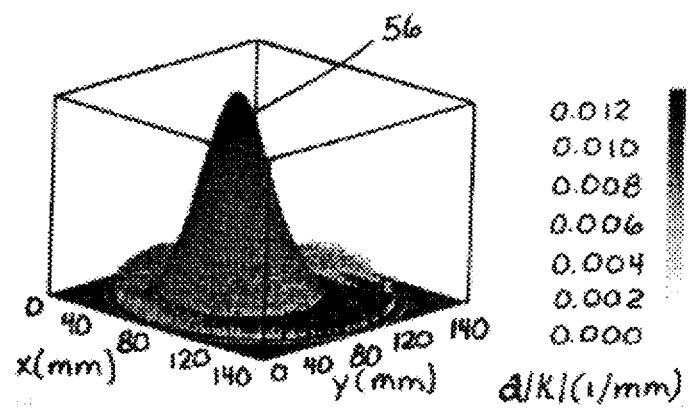
Figure 16C:
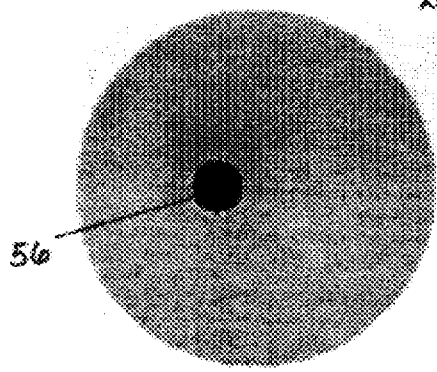
Figure 16D:
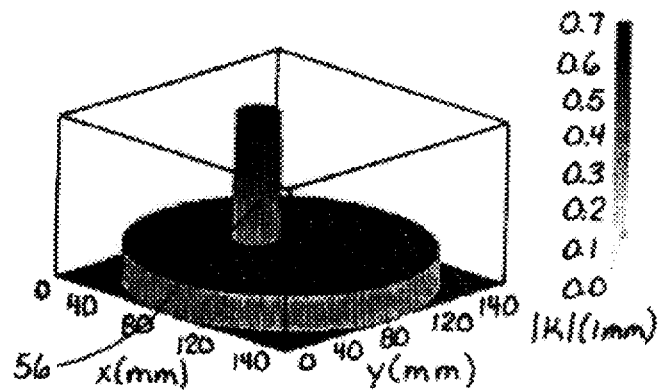
Figure 17:
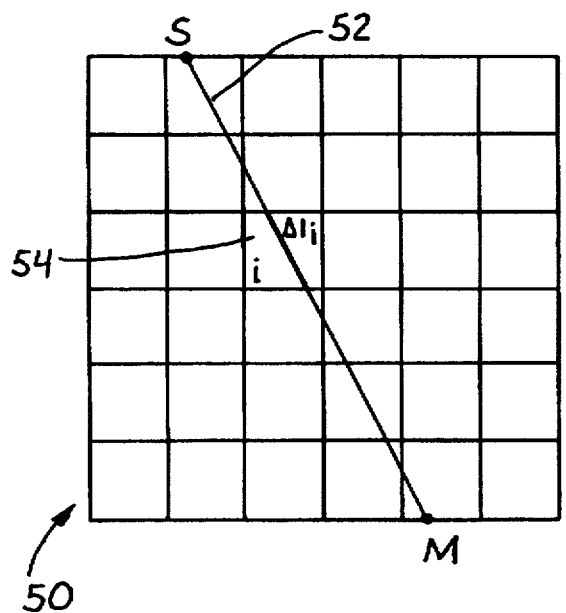
FIG. 17 is a diagram illustrating the partitioning of space to produce a lattice of pixels used in the reconstruction methodology of the invention and the precise meaning of the line element $\Delta l_i$ within each pixel cell.

The invention and its various embodiments can now be better understood by turning to the following detailed description.

DETAILED DESCRIPTION OF THE PREFERRED EMBODIMENTS

Non-invasive near infrared optical medical imaging device for both hematoma detection in the brain and early tumor detection in the breast is achieved using WKB image reconstruction which allows a mapping of the position dependent optical absorption and scattering coefficients in the tissue at near infrared wavelengths using measured optical signals on the tissue boundary. Spatial resolutions in the range of 5 mm turn for adult brain sizes and breast sizes can be achieved. The detectability limit for breast tumor imaging of about 2 mm may also be achievable with method of the invention. The image reconstruction utilizes WKB approximation on the most probable diffusion paths, which to first order approximation are the straight line-of-sight paths, between the plurality of sources and the plurality of detectors. The WKB approximation yields a set of linear equations in which the contrast optical absorption coefficients are the unknowns and for which signals can be generated to produce a pixel map of the contrast optical resolution of the scanned tissue.

The methodology of the invention is formulated in the frequency domain rather than in the time domain, as the case with many prior art near infrared imaging methodologies. The methodology of the invention sums up some of the important photon diffusion paths. The methodology provides valid results when the absorption coefficient varies in space smoothly. The methodology is an approximation beyond the first order of perturbation (Born approximation) approach and contains all orders of the variations in the absorption coefficient or scattering coefficient in the approximation. The images are reconstructed more accurately at higher modulation frequencies, limited only by the lower signal-to-noise ratio which is obtained the higher the modulation frequency used.

The opto-electronic system, generally denoted in FIG. 3 by reference numeral 17, used in connection with the present methodology is substantially the same as used in other current near infrared systems. In the diagrammatic depiction of FIG. 2 and FIG. 3, an idealized cylindrical or spherical tissue mass or target 12 has a circular ring 14 of spatially separated receiving optical fiber bundles disposed on a diameter R about target 12 and coupled to a corresponding plurality of near infrared detector positions 16. (In this initial design, in order to save cost, a single ultra-sensitive near infrared detector is used to scan light from the plurality of receiving fiber bundles. Later this will be generalized to include include a plurality of near infrared detectors to improve scanning speed.) The radius, R, is chosen in the illustrated embodiments discussed below to approximate the size of a human brain or breast. However, any size or shape target may be utilized in connection with the invention, up to the limit of sensitivity of the near infrared detector. Insofar as cross-sectional data is concerned, cylindrical or spherical models and their corresponding data can be regarded as at least qualitatively equivalent.

Tissue mass 12 is irradiated with near infrared light from a plurality of source positions. The present optical coupling system on the source side is comprised of a plurality of optical fibers 27 azimuthally equidistantly disposed on a diameter of ring 14 about target 12 and coupled to a modulated near infrared laser 19 through a light distributor 18 and a light chopper 21 and an optics focusing system 23. Distributor 18 is a conventional optomechanical system for rotating a mirror to distribute the laser beam among a plurality of optical fibers 27. The mirror of distributor 18 is driven by a motor 25 controlled by a motor controller 29, whose operation is synchronized with a computer data acquisition and processing control circuit 31. Circuit 31 also controls a motor control circuit 33 which controls a stepping motor 37. Stepping motor 37 translates a detector 16 on a screw drive 39 so that detector 16 is positioned behind a selected one of a plurality of receiving optical fiber bundles 35. Optical fiber bundles 35 are equally azimuthally spaced about ring 14. Detector 16 is driven in sequence across the transmitting ends of fibers 35 and generates an array of received data signals which is coupled to demodulator and control circuit 41. Demodulator and control circuit 41 demodulates the modulated data signal and generates appropriate timing and control signals for computer data acquisition and processing control circuit 31 by which the sequencing and synchronization of the light distribution to optical fibers 27 and 35 are controlled according to the protocols described below. Photons are injected from the source fibers 27 into the tissue mass 12 and collected by the detector fiber bundles 35 on the ring 14. Signals from the plurality of fibers 35 to detector 16 are then input into a computer 20 through front-end electronics 41, which processes the signals according to the methodology described below to display a near infrared tomograph on a computer monitor, printer or other equivalent output device.

Various classes of light sources are presently preferred. In the embodiment illustrated in FIG. 3 a single laser source 19 distributed into an array through optical fibers and a single light detector 16 collecting signals through an optical fiber bundles has been described. However, it is also contemplated that a plurality of laser sources and detectors could be equivalently substituted in order to speed up the scanning process. For example, laser diodes in wavelength of 700 to 900 nanometers with power ratings of 30 milliwatts are readily commercially available. In the embodiment of FIG. 3, array 14 of diodes 19 are excited at periodically discrete frequencies and cover a plurality of steps, for example eight, in a range of 10 to 500 MHz. The modulation could either be square wave or sinusoidal superimposed on a DC level. It is contemplated that arrays including between 32 to 128 laser diodes will serve as practical image illuminators.

Various classes of light detectors 16 are also presently preferred. Since the intrinsic signal-to-noise ratio is determined by the performance of the photodetector, and is likely to be the most critical element in the near infrared scanning system, it is contemplated that many different types of technologies may be used. Photomultiplier tubes 16 with gallium-arsenide or galliam-arsdenide-phosphate photocathodes manufactured by Hamamatsu or Intervac, avalanche photodiodes made by Advanced Photonix, or Radiation Monitor Detector, or EG & G, and Generation III image intensifiers made by Intervac or Hamamatsu coupled with charge-coupled-device (CCD) cameras are currently considered as the preferred choices.

Photodiode detectors using gallium-arsenide or gallium-arsenide-phosphate for near infrared detection have been developed in night vision goggles. MCP photomultiplier tubes and photomultiplier tubes with gallium-arsenide or gallium-arsenide-phosphate photocathodes and multi-channel Dynode/Anode seem ideal for brain scanner applications of the invention, although the photomultiplier tubes have the disadvantage of relatively high cost of such devices. On the other hand, avalanche photodiodes are more economical, and have a sensitivity of close to 100% quantum efficiency. Avalanche photodiodes have the advantage of eliminating the need for high voltage power supplies with its attendant expense and hazard. Generation III image intensifiers are also available for low frequency modulation or DC level near infrared measurements. CCD cameras have been showing a remarkable improvement recently. By cooling them, one can reduce noise level significantly, allowing the high quantum efficiency of CCD itself to be fully utilized. For a reasonably small body part such as the breast, this detector will provide not only enough signal-to-noise ratio but the best position resolution available today.

The front end electronics 31 coupled to the photomultiplier tubes or other types of photo detectors 16 in the illustrating embodiment includes a buffer amplifier, the output of which is connected to two integrated circuits, Gilbert cell, double balance mixers whose reference signals are in quadrature phase. The reference and driving frequencies are the same. The phase of the diffused infrared signals arriving at the photo detectors can be measured utilizing the quadrature phase reference signal to improve image resolution. The output of the mixer is passed through a low pass filter, which then gives narrow band detection at the same frequency as the excitation.

The photodiode light sources 19 are sequentially excited in both frequency and time. In the embodiment where a plurality of detectors 16 are employed instead of a single detector, the entire output of the detector array can be simultaneously read. In this way, only one detection frequency is generated at a time. At each frequency, the time sequence of excitation around the ring of light emitting diodes 16 is used to indicate which source is active at a given time. For a system of 32 photomultiplier detectors 32 for example, this arrangement requires 32 quadrature detection receiving channels. Once the excitation has been sent to all diodes 19 at one of the frequencies, a new modulation frequency will be chosen and the cycle repeated.

Integrated circuit analog-to-digital converter positioned close to detectors 16 can be used to convert the output to a digitized signal coupled to computer 20 over a digital parallel interface bus. Alternatively, analog signals can be directly coupled from array 14 to computer 20 and digitized with an analog input board connected to the computer bus. Once the signals are converted to digital form, the data is processed in a conventional personal computer.

Before the implementation of the reconstruction methodology is described, a discussion of the mathematical model used to describe light diffusion and the solution to the light diffusion equation using the WKB approximation, which is well-known from quantum mechanics and quantum field theory, would be helpful. When the light source is treated as isotropic, the time dependent diffusion equation is in the form of Equation (2) below:

$$\frac{1}{c}\dot{\phi}(x,t) = \nabla \cdot [D(x)\nabla\phi(x,t)] - \mu_a(x)\phi(x,t) + \eta(x,t), \quad (2)$$

where $\phi(x,t)$ is the diffuse photon fluence rate proportional to the energy density, $\mu_a(x)$ is the position dependent absorption coefficient to be imaged, $\eta(x,t)$ represents the isotropic light source, and $D(x)$ is the position dependent diffusion coefficient, also to be imaged, which is related to the scattering coefficient via Equation (3) below:

$$D(x) = \frac{1}{3[\mu_a(x) + \mu_s'(x)]}, \quad (3)$$

where $\mu_s'(x) = (1-g)\mu_s(x)$ is the position dependent transport (or reduced) scattering coefficient with g being the mean cosine of the scattering angle. In tissue media the transport scattering coefficient $\mu_s'$ is much greater than the absorption coefficient $\mu_a$, thus the diffusion coefficient D is essentially given by $1/3\mu_s'$.

In most of this discussion, for the sake of simplicity and clarity, D is treated as constant. Extensions to the case where D also varies in space will be made approximately at the end, in Equations (23) and (27).

Consider first the source function describing the isotropic source of light as a point source at position a and a sharp pulse at time t=0 (the time domain formulation) described by the product of the spatial and temporal Dirac delta functions below in Equation (4).

$$\eta(x,t) = \delta(x-a)\delta(t), \quad (4)$$

The solution to the diffusion Equation (2) for a homogeneous medium, i.e. where the absorption coefficient $\mu_a(x)$ and the transport scattering coefficient $\mu_s'(x)$ do not vary in space, corresponding to a pulsed, point source is readily solved using Fourier transforms and is given by Equation (5) below.

$$\phi_0(x,t;a,0) = \left(\frac{1}{4\pi Dt}\right)^{3/2} \exp\left(-\frac{(x-a)^2}{4Dt} - \mu_a t\right). \quad (5)$$

In general, $\mu_a(x)$ is position dependent, and the solution to the diffusion equation, assuming a constant D, can be written as a path integral, following Feynman, given by Equation (6).

$$\phi(b,t;a,0) = \int Dx(\tau)e^{-s\{x(\tau)\}}, \quad (6)$$

where $\int Dx(\tau)$ denotes a path integral over all possible diffusion paths described by the trajectory $x(\tau)$, with $0 \leq \tau \leq t$ as a running time variable, and the action function, $S\{x(\tau)\}$ being given by Equation (7) below.

$$S\{x(\tau)\} \equiv -\int_0^t d\tau \left(\frac{\dot{x}(\tau)^2}{4D} + \mu_a(x(\tau))\right) \quad (7)$$

Thus, the photon diffusion problem has the following simple analog in classical mechanics, namely a point mass moving in potential $-\mu_a(x)$ with a mass $1/(2D)$. Using the well known stationary phase approximation, the lowest order photon fluence function $\phi(x,t)$ is determined by minimizing the action $S\{x(\tau)\}$, which determines what shall be defined as the most probable diffusion path of the equivalent "classical" particle, with the starting point (x=a, at τ=0) and ending point (x=b, at τ=t). The equation of motion for the analogous classical particle is then given by Equation (8) below.

$$\frac{1}{2D}\ddot{x} - \nabla\mu_a(x) = 0. \quad (8)$$

Once the most probable diffusion path $\bar{x}(\tau)$ is found, the action in Equation (6) can be expanded around this path, the result of which is given below in Equation (9).

$$S\{x(\tau)\} = S\{\bar{x}(\tau)\} + \frac{1}{2!} \delta^2 S + \text{higher orders}. \tag{9}$$

Performing the integration up to the $\delta^2 S$ order, the semi-classical or WKB approximation for the diffusive photon fluence function is found below in Equation (10).

$$\phi(b,t;a,0) = \sqrt{\left| \det\left( -\frac{1}{2\pi} \frac{\partial^2 \bar{S}}{\partial a \partial b} \right) \right|} \exp(-\bar{S}), \tag{10}$$

where $\bar{S} \equiv S\{\bar{x}(\tau)\}$.

Now it can be appreciated that retaining a second order variation in Equation (9) is equivalent to the WKB approximation in quantum mechanics and quantum field theory. This point will become even clearer when the problem is re-formulated in the frequency domain. Further, Equation (10) contains not only the contribution from the most probable diffusion paths, but also paths close to it, corresponding to the quasi ballistic (or snake) photon paths or those inside the banana shaped region around the most probable diffusion path. This is manifested in the integration of the $\delta^2 S$ term, which gives rise to the determinant correction factor in Equation (10). This determinant can be thought of as the density of paths adjacent to the most probable diffusion path. In fact, for a homogeneous medium, the solution of Equation (8) gives a straight line between a and b, as shown in Equation (11) below.

$$x = a + \frac{\tau}{t}(b-a). \tag{11}$$

Putting the solution of Equation (11) into Equation (10) gives the exact diffusion propagator in homogeneous medium which was described in Equation (5).

The WKB approximation can be re-formulated in the frequency domain where the time at the ending point need not be specified and the most probable diffusion path satisfies an equation which is easier to handle than Equation (8). Experimentally, the frequency domain is achieved by amplitude modulating a continuous wave light source, or by performing a Fourier transform on the time domain signal generated from a pulsed source (4). This corresponds to a new source function for the light source given by the expression below in Equation (12).

$$\eta(x,t) = \delta(x-a) e^{-wt}. \tag{12}$$

For a homogeneous medium, the diffusion Equation (2) can be solved using Fourier transform to provide the diffusion propagator described in Equation (13) below.

$$\phi_0(x,a,\omega) = \frac{1}{4\pi D r} e^{-\kappa r}, \tag{13}$$

where the diffusive propagation constant $\kappa \equiv \kappa(\omega)$, a complex variable, is related to the absorption and scattering coefficients according to Equation (14).

$$\kappa(\omega) = \kappa'(\omega) - i\kappa''(\omega), \tag{14}$$

$$\kappa'(\omega) = \frac{1}{\sqrt{2D}} (\sqrt{\mu_a^2 + \omega^2} + \mu_a)^{1/2},$$

$$\kappa''(\omega) = \frac{1}{\sqrt{2D}} (\sqrt{\mu_a^2 + \omega^2} - \mu_a)^{1/2},$$

which $\kappa^2(\omega) = (\mu_a - i\omega)/D$.

Equation (13) for the diffusion propagator provides that the diffusive absorption length is equal to $1/\kappa'(\omega)$, which means that the effective absorption length is frequency dependent and decreases as the frequency increases for a fixed value of the absorption coefficient $\mu_a$. Thus at a fixed distance, r, to the source, increasing modulation frequency $\omega$ leads to an exponential decrease in the number of detectable photons at that frequency.

For the more complex case of an inhomogeneous medium with position dependent absorption coefficient $\mu_a(x)$, the WKB approximation to the frequency domain photon fluence function $\phi(b, a, \omega)$ for a source given in Equation (12) can be obtained through Fourier transform and expressed by Equation (15).

$$\phi(b,a,\omega) = \int_{-\infty}^{\infty} dt \sqrt{\left| \det\left( -\frac{1}{2\pi} \frac{\partial^2 \bar{S}}{\partial a \partial b} \right) \right|} e^{-\bar{S}(b,a,t) + \omega t}, \tag{15}$$

where $\bar{S}(b,a,t)$ is the time-domain classical action corresponding to the most probable diffusion path. Applying the stationary phase approximation technique from statistical mechanics, a special time scale $t_0$ can be identified through Equation (16).

$$\frac{\partial \bar{S}(b,a,t_0)}{\partial t} = i\omega. \tag{16}$$

Therefore, the process of going from time domain with t being the independent variable to frequency domain with $\omega$ being the independent variable corresponds to a standard Legendre transformation. The Green's function in the frequency domain in the WKB approximation can, thus, be written below as set forth in Equation (17).

$$\phi(b,a,\omega) = \tag{17}$$

$$\left(\frac{1}{2\pi}\right)^{-\frac{d-1}{2}} \sqrt{\tilde{D}} \exp(-\int \kappa(x,\omega) dl) \equiv \left(\frac{1}{2\pi}\right)^{-\frac{d-1}{2}} \sqrt{\tilde{D}} e^{-w(b,a,\omega)},$$

where dl is a path element, $W(b,a,\omega)$ is equal to $\int_a^b \kappa(x,w) dl$ and path's density pre-factor $\tilde{D}$ is given by Equation (18).

$$D = \det\left( -\frac{\partial^2 S}{\partial a \partial b} \right) / \frac{\partial^2 S}{\partial t^2} = \det \begin{bmatrix} \frac{\partial^2 w}{\partial a \partial b} & i \frac{\partial^2 w}{\partial a \partial \omega} \\ i \frac{\partial^2 w}{\partial b \partial \omega} & -\frac{\partial^2 w}{\partial \omega^2} \end{bmatrix}. \tag{18}$$

The frequency domain most probable diffusion path is defined by Equation (19) below.

$$\delta W(b,a,\omega) = \delta \int_a^b \kappa(x,\omega) dl = 0. \tag{19}$$

Since $\kappa(x,\omega)$ is complex, this equation is true for both the real and imaginary parts of $\kappa(\omega)$. Explicit form of the frequency domain most probable diffusion path can be obtained using geometrical calculus. Denoting t, n as the unit tangential and principle normal vectors of the most probable diffusion path respectively, letting R be the local radius of curvature of the most probable diffusion path, these quantities can be related the trajectory function of the most probable diffusion path, x(l), by Equation (20) below.

$$t = \frac{dx}{dl}, \quad \frac{n}{R} = \frac{d^2 x}{dl^2}. \tag{20}$$

The most probable diffusion path in the frequency domain is then determined by Equation (21) below.

$$\nabla\mu_a - (\hat{t}\cdot\nabla\mu_a)\hat{t} = (\nabla\mu_a)_n \hat{n} = 2\sqrt{\mu_a^2 + \omega^2}\ \frac{\hat{n}}{R}\quad(21)$$

It is to be emphasized that Equation (21) applies to the case of constant diffusion coefficient D with the absorption coefficient $\mu_a(x)$ being the only position dependent variable. Generalization to the case in which both D(x) and $mu_a(x)$ vary in space are given below in Equations (24) and (28).

An interesting qualitative feature of Equation (21) is that for a fixed spatial distribution of the absorption coefficient, the radius of curvature, R, of the most probable diffusion path becomes larger, that is as the most probable diffusion path straightens out, as the modulation frequency $\omega$ increases. Analytic solutions of Equation (21) for an arbitrary absorption coefficient $\mu_a(x)$ can be difficult to obtain. However, it is possible to numerically trace out a most probable diffusion path in the frequency domain through Equation (21). Once this path is obtained, numerical integration of $\kappa(x,\omega)$ along the path can be performed and the photon fluence function obtained in the WKB approximation at the end-point or detector position x=b through use of Equation (17).

The important condition for determining the regime of validity for the WKB approximation in the frequency domain is given by the inequality in Equation (22) below.

$$\left|\frac{\nabla^2 S}{(\nabla S)^2}\right| = |\nabla \kappa^{-1}| = \frac{\sqrt{D}}{2}\ \frac{|\nabla\mu_a|}{(\mu_a^2 + \omega^2)^{3/4}} \ll 1.\quad(22)$$

For a given distribution of absorption coefficient $\mu_a(x)$, the approximation becomes better at higher modulation frequencies. This can be associated with the fact that as the modulation frequency increases, the effective absorption length decreases, leading to a shrinkage in the width of the banana shaped region connecting the source and the detector in which photon diffusion paths are concentrated. This shrinkage implies that the most probable diffusion path carries more and more weight in determining the photon flux at the detector position at higher modulation frequencies. Hence, the WKB approximation becomes better as the modulation frequency increases.

The analytical method just described assumes that the optical absorption coefficient as a function of position is known and the optical fluence is then found given a known light source. Near infrared tomography, however, is just the opposite, namely, the inverse problem, must be solved. In this case the source intensity and the detected photon fluence at the sample boundary are known and what must be determined is the position dependent optical absorption coefficient. The difficulty lies in the fact that in order to relate the absorption coefficient as a function of position inside the tissue to the measured light intensity at some tissue surface position b, given a source location a on another point of the tissue surface, it is necessary to know the most probable diffusion path $\bar{x}(\tau)$ in the time domain or $\bar{x}(l)$ in the frequency domain. But the shape of the most probable diffusion path itself is determined by the distribution of optical absorption which is unknown. At present, no general solution to this "chicken-and-egg" problem. However, when the inhomogeneity can be regarded as small relative to the background medium, a perturbative solution at the level of the action, but not the optical fluence function, can be found. This key difference sets the WKB approximation method, described above, upon which the invention is based, apart from other current imaging methodology, and allows efficient, robust, and elegant near infrared image reconstruction to be performed.

Define a background or reference homogeneous tissue medium with optical absorption coefficient $\mu_{ao}$ and transport scattering coefficient $\mu'_{so}$ with the corresponding diffusion coefficient $D_0$. Strictly speaking these parameters should correspond to the spatial average of those in the inhomogeneous medium to be imaged. In practice, one may set them to be the normal tissue parameters for the brain or breast of a typical person. From Equation (14), the diffusive propagation constant $\kappa_0$ for the reference homogeneous medium may be obtained for a given modulation frequency. Spatial inhomogeneities in the absorption and scattering properties are now summarized in $\delta\kappa(x) \equiv \kappa(x) - \kappa_0$. Since the photon flux for given positions of the source (a) and the detector (b) for the reference homogeneous medium can be easily computed, the WKB approximation for the inhomogeneous tissue medium, summarized by Equation (23), may be further simplified to give Equation (23) below.

$$\int_a^b \delta\kappa(x)dl = \ln(J_O(b,a,\omega)/J_M(b,a,\omega)),\quad(23)$$

where $J_O$ is the detected photon flux for the reference homogeneous medium, and $J_M$ is the measured photon flux for the inhomogeneous medium to be imaged. The line integration should be taken along the most probable diffusion path for the inhomogeneous medium. It is to be emphasized that Equation (23) applies in the general situation in which both $\mu_a(x)$ and $\mu'_s(x)$ vary in space. The corresponding equation governing the most probable diffusion path is modified from Equation (21) to Equation (24) below.

$$(\nabla\kappa)_n = \frac{\kappa}{R},\quad(24)$$

The condition for the validity of Equation (23) is $$\nabla D/D_0 \ll |\kappa_0|,\quad(25)$$

If the inhomogeneity is considered small, one may take to first approximation the most probable diffusion path for the reference homogeneous medium, which is simply the straight line-of-sight between the source and the detector. In all the sample image reconstruction shown in FIGS. 5–16 from computer generated diffusion equation forward data, such an approximation has been taken.

In a more sophisticated embodiment of the invention, the straight line-of-sight approximation to the most probable diffusion path may first be used to find the first order approximate solution for the contrast diffusive propagation constant, $\delta\kappa_1(x)$, using Equation (23). Then this first order solution may be used to find corrections to the most probable diffusion path. Then apply this corrected most probable path to solve for the second order solution, $\delta\kappa_2(x)$, using again Equation (23). Iterate this procedure until the solution becomes self-consistent, namely when the most probable path converges to a final shape. This iterated solution will lead to improved image resolution.

Equation (23) should be taken as a complex equation. The real part of the Equation corresponds to a relation between the real part $\kappa'(x)$ and the logarithm of the ratio of detected photon flux which is also known as the modulation. The imaginary part of Equation (23) corresponds to a relationship between $\kappa''(x)$ and the contrast between the phase shift of the frequency domain detected photon flux (relative to the light source) for the inhomogeneous medium and that of the reference homogeneous medium.

Equation (23) applies to any boundary condition at the sample surface, since the effect of boundary condition is automatically taken into account by the use of appropriate photon flux for the reference homogeneous medium.

Discretizing Equation (23) onto a pixel lattice inside the tissue medium leads to Equation (1) given in the Brief Description section above.

For illustration purposes, the special case in which D is a constant and only the absorption coefficient varies in space can be considered more closely. Linearizing Equation (23) to first order in $\delta\mu_a(x) \equiv \mu_a(x) - \mu_{a0}$ leads to Equation (26) below.

$$\ln[J_0(b,a,\omega)/J_M(b,a,\omega)] = \frac{\kappa_0^*}{2\sqrt{\mu_{a0}^2 + \omega^2}} \int_a^b \delta\mu_a(x)dl, \quad (26)$$

Equation (26) provides for methodology for image reconstruction of the position dependent absorption inefficient directly in the case of constant diffusion constant D (or constant scattering coefficient $\mu'_s$).

In the case in which D(x) varies in space, the general equation governing the principle of WKB image reconstruction, Equation (23), may be linearized to yield below Equation (27) in terms of $\delta\mu_a(x)$ and $\delta D(x)$ directly.

$$\ln[J_0(b,a,\omega)/J_M(b,a,\omega)] = \frac{\kappa_0^*}{2\sqrt{\mu_{a0}^2 + \omega^2}} \int_a^b \delta\mu_a(x)dl - \quad (27)$$

$$\frac{\kappa_0}{2D_0} \int_a^b \delta D(x)dl.$$

Discretizing Equation (27) on a pixel lattice, one can reconstruct images of both $\delta\mu_a(x) = \mu_a(x) - \mu_{a0}$ and $\delta D(x) = D(x) - D_0$. The most probable diffusion path is determined in this case by Equation (28) below.

$$\frac{(\nabla\mu)_n}{\sqrt{\mu_a^2 + \omega^2}} - \frac{(\nabla D)_n}{D} = \frac{2}{R}, \quad (28)$$

where the subscript n represents the normal component and R is the curvature radius of the most probable diffusion path, respectively.

Image reconstruction of a target in which photon migration process is diffusive, of either the contrast diffusive propagation constant $\delta\kappa(x)$ using Equation (23), or the contrast absorption coefficient $\delta\mu_a(x)$ and contrast diffusion coefficient $\delta D(x)$ using Equation (27), in the case when both the absorption and scattering coefficients vary in space, or the contrast absorption coefficient $\delta\mu_a(x)$ alone using Equation (26) when the scattering coefficient (or diffusion constant) is treated as a constant, as the signal processing method, is defined for the purposes of this specification as a "WKB image reconstruction".

As discussed above, the WKB result is more accurate at higher modulating frequencies, since the higher the frequency, the straighter the mean probable diffusion path. Therefore, by increasing the modulation frequency, Equation (26) may be used to increase image resolution which would be of high utility for early detection for malignant breast tumors.

The higher spatial resolution comes at the price of a decrease in the number of photons revived at the detector. The number of photons received decreases exponentially as the frequency increases which results in a lower signal-to-noise ratio. Thus, the practical limitation in the spatial resolution of a near infrared breast scanner will probably not arise from the fundamental physical laws governing photon migration in human tissue, but instead will come from the limited signal-to-noise ratio of the detector, since the magnitude of the laser power source cannot be increased indefinitely without causing biological damage to the tissue.

The WKB method approximates the action to the first two lowest orders. Therefore, the Green's function contains all orders for the variation of the absorption coefficient, thus, making the WKB method an intrinsically better approximation than simple perturbation methodology which approximates the Green's function only to the first order in the variation in optical absorption coefficients.

Consider now the images reconstructed from computed mock data, as a test of the performance of the WKB image reconstruction methodology. The mock data in most cases correspond to numerical forward solutions of the diffusion equation for a turbid medium of cylindrical geometry containing a number of absorbing cylinders with their axes parallel to that of the medium. In initial studies, a single sphere placed in an infinite medium geometry was used. Since an exact solution to the diffusion equation is available for such a simple geometry, this simplest geometry allows an "ideal" set of mock data to be generated for testing the WKB image reconstruction methodology. A sample image in this infinite-space geometry is given in FIG. 4(a)–(d). The spherical inclusion has a radius of a=10 mm and is located at (−35 mm, 0). The image is reconstructed on a 40×40 lattice. The modulating frequency used to produce all the forward data is chosen to be f=200 MHz The image shows a spatial resolution better than ≈0.5 cm. The source and detectors are placed on an imaginary circle, which is in a plane containing the center of the included sphere.

Consider now the more experimentally relevant finite geometry. FIG. 2 defines a finite cylindrical model tissue geometry with an absorbing boundary which models actual tissue medium more realistically, and contains multiple cylindrical inclusions as models for hematomas or tumors. The forward mock data are generated by numerically solving the two-dimensional diffusion equation using a finite difference method involving Newton's forward difference formula. The "measured" mock data are the photon fluxes, $J = -D\nabla\phi|_s$, at the various detector positions.

The radius of the cylinder is chosen to be R=70 mm for all brain scanner simulations. For breast scanner simulations, a size of R=50 mm is used. The photon fluxes are computed at 64 equally spaced detector positions on the half circle opposite to each of the 128 sources (equally spaced and on the whole circle); e.g., if the source is at θ=0, then detectors are placed uniformly within the angular range $$\left[\frac{\pi}{2}, \frac{3\pi}{2}\right].$$

The modulating frequency used to produce all the forward data is chosen to be f=200 MHz.

For brain scanner simulations, the optical parameters for the reference homogeneous medium are chosen to correspond realistically to those of white matter: $\mu_{a0}$=0.003 mm$^{-1}$, and $\mu'_{a0}$=1.6 mm$^{-1}$. The absorbing sphere or cylinders is assumed to have optical parameters corresponding to those of a realistic hematoma, with $\mu_{a1}$=0.1 mm$^{-1}$, and $\mu'_{s1}$=1.6 mm$^{-1}$. [Absorption coefficient for hematoma seems to vary widely from different sources in the literature. Here a conservative approach has been taken such that the value of $\mu_a$ roughly one-third of the average value for pure blood is used.]

Note that in all of the preceding formulas the light speed has been taken to be unity. In the actual computation, this simplification is easily removed by dividing the modulation frequency ω by $c=c_0/1.33=2.26\times10^{10}$ cm/s.

FIG. 5(a)–(d) shows a test image reconstructed for a sample of size of R=70 mm (corresponding to an adult brain), whose geometry is depicted in FIG. 2. The modulating frequency and the optical parameters are the same as those in FIG. 4(a)–(d). The radii of the three inclusions are $a_1=a_2=a_3=10$ mm and their center locations are $O_1=(-20$ mm, 20 mm), $O_2=(20$ mm, 20 mm) and $O_3=(0, 20$ mm) in forward data generation. The image is reconstructed on a 40×40 lattice.

FIG. 6(a)–(d), 7(a)–(d), and 8(a)–(d) are images reconstructed using the same data as in FIG. 5(a)–(d) except that random Gaussian random noises are added to the data, in order to test the robustness of the WKB image reconstruction methodology against signal noise. The three images correspond, respectively, 10%, 20%, and 30% noise levels, defined as the root mean square of the noise statistics divided by the signal at a given detection point in homogeneous medium, i.e., in the absence of absorber inclusions. Observe that satisfactorily the WKB method is quite resistant to signal noise.

Starting in FIG. 9(a)–(d), the performance of WKB image reconstruction method is tested for breast scanner applications. Here the size of the samples are taken to be R=50 mm, corresponding to that of a realistic female breast. The modulating frequency is again taken f=200 MHz. The background optical parameters are chosen as $\mu_{a0}=0.008$ mm$^{-1}$, and $\mu'_{s0}=1$ mm$^{-1}$. For the absorbing cylinders, which model cancerous tumors, $\mu_{a1}=0.024$ mm$^{-1}$, and $\mu'_{s1}=1$ mm$^{-1}$ are taken. The image is again reconstructed on a 40×40 lattice. Here it is observed that the reconstructed circle size is quite a bit larger than that used in generating the forward data and, at the same time, the reconstructed $\delta\mu_a$ is quite a bit smaller than the actual value used for generating the forward data (also compare with FIG. 5(a)–(d) for the brain hematoma case). This represents a systematic error in the WKB method. This is perhaps due to the use of the simplest straight line-of-sight approximation of the most probable diffusion path. Inclusion of curved most probable diffusion paths using an iteration scheme may lead to improvement of the image resolution in order to achieve optimum resolution for smaller size inclusions such as in FIG. 9(a)–(d). As can be seen from FIG. 5 and FIG. 9(a)–(d), the current spatial resolution that can be achieved is on the order 0.5 cm.

FIG. 10(a)–(d) and 11(a)–(d) are images reconstructed using the same mock data as in FIG. 9(a)–(d) except that Gaussian random noises are added to the data. The two images correspond, respectively, 5% and 10% noise levels. It is observed that for smaller inclusions (compared to those in FIG. 5(a)–(d), noise has a bigger effect on the image quality here, since the contrast in $\mu_a$ is 10 times smaller for breast than for brain.

FIG. 12(a)–(d) is a test image for breast application with two cylindrical inclusions of radius $a_1=5$ mm at (15 mm, 15 mm) and $a_2=5$ mm at (−20 mm, −20 mm). Other parameters are the same as those in FIG. 9(a)–(d). In the next two figures the robustness of image reconstruction against background fluctuations (static) in $\mu_a$ is tested. The average of $\mu_{a0}$ has the same value as that in FIG. 12(a)–(d), i.e., $(\mu_{a0})=0.008$ mm$^{-1}$, but the variation in $\mu_{a0}(x)=(\mu_{a0})+\delta\mu_a(x)$ satisfies $$\langle\delta\mu_a(x)\delta\mu_a(x')\rangle=\Delta^2 \exp[-(x-x')^2/\lambda^2].$$

The forward data are generated in the presence of spatial correlations in $\mu_a$. FIG. 13(a)–(d) corresponds to $\Delta/(\mu_{a0})=$ 3% and FIG. 14(a)–(d) corresponds to $\Delta/(\mu_{a0})=15\%$. The correlation length in both images is chosen as $\lambda=\sqrt{D/\mu_{a0}}\approx6.4$ mm.

The above figures are all reconstructed using the more limited image reconstruction scheme of Equation (26) which assumes the diffusion constant D is a constant. The two figures below are shown to illustrate the use of the more general image reconstruction scheme for the contrast diffusive propagation constant δκ(x). These two figures are also generated using the more powerful SART method (to be discussed below) for solving the resultant linear equations.

FIG. 15(a)–(d) shows the reconstructed cross-sectional image of the contrast diffusive propagation constant δκ(x), using Equation (1), from computer generated mock data. The geometry is an infinite tissue medium containing a single spherical model hematoma with a=10 mm at (15 mm, 0. mm). Sources and detectors are placed on an imaginary circle with radius R=70 mm. The optical parameters used are $\mu_{a0}=0.003$/mm, $\mu_{a1}=0.10$/mm, $\mu_{s0}=\mu_{s1}=1.6$/mm. The lower figures are for the input κ values using two different graphical representations. The top figures are the reconstructed images. The SART method is used for the real part of the δκ(x) only. The modulation frequency f=200 MHz is used. The pixel lattice of 128×128 is used. No signal noise is included.

FIG. 16(a)–(d) is the reconstructed cross-sectional image of FIG. 15 except both real and imaginary parts of κ(x) are used here for image reconstruction. The plotted images are for the absolute value of the complex contrast diffusive propagation constant δκ(x).

Test images given above show the essential robustness of the WKB image reconstruction methodology to noise and to background fluctuations. This leads one to believe that the new WKB imaging methodology on the invention will give birth to clinically viable NIR imaging devices. It is reasonable to believe that images of similar quality can also be obtained using red experimental data rather than computer generated mock data, since the diffusion equation is a rather realistic description of the photon migration process in human tissue.

The WKB image reconstruction methodology of the invention, a source code listing of which is filed as Appendix 1 with the application and included in the file history of this application, available for public examination, allows the mapping of the position dependent optical absorption coefficient and scattering coefficient at near infrared frequencies in the range of 700 to 900 nanometers with spatial resolutions in the range of 5 mm for adult brain sizes and breast sizes. The use of other programs for implementing and improving graphic representations are contemplated as being included within the scope of the invention.

Linear equations (23) or (26) are solved using a single value decomposition (SVD) technique which is a conventional numerical technique for the solution of linear equations when the number of unknowns is less than the number of equations.

Besides the SVD technique, there are other methods for solving linear equations (1), or discretized versions of (26), or (27). In particular, it has been reported that the simultaneous algebraic reconstruction technique (SART) generates images with good quality with a single iteration. In essence, the ART algorithm is an iterative procedure which contains the following: guess a solution $\delta\mu_{ai}$ (a point in the hyperspace), project the guess solution $\delta\mu_a$ onto one of the hyperplanes represented by Equation (1) to obtain a new solution, and then repeat this procedure. The basic premise of SART includes the following features: (i) Bilinear elements are chosen over the traditional pixel basis to reduce the "salt and pepper" noise in the image. (ii) The correction to the guess solution is found by simultaneously considering all linear equations resulting from the use of Equation (1) for various pairs of source and detection positions to further reduce the noise. (iii) A Hemming window is used to emphasize the corrections applied near the middle of a path.

To implement the SART method, a path J is divided into $M_j$ equidistant sections $$\sum_{m=1}^{M_j} \hat{\mu}_a(l_{jm}) \Delta l = p_j, \quad (29)$$

where $p_j$ is the right side of Equation (1). The value $\hat{\mu}_a(l_{jm})$ is determined from $\delta\mu_{ai}$ on the neighboring points of the lattice by bilinear interpolation $$\hat{\mu}_a(l_{jm}) = \sum_{i=1}^{N} d_{jim} \delta\mu_{ai}. \quad (30)$$

Thus, $$p_j = \sum_{m=1}^{M_j} \sum_{i=1}^{N} d_{jim} \delta\mu_{ai} \Delta l \equiv \sum_{i=1}^{N} a_{ji} \delta\mu_{ai}. \quad (31)$$

The SART iterative solution is $$\delta\mu_{ai}^{(k+1)} = \delta\mu_{ai}^{(k)} + \sum_j \left( t_{ji} \frac{p_j - \sum_i a_{ji} \delta\mu_{ai}^{(k)}}{\sum_i a_{ji}} \right) / \sum_j a_{ji}, \quad (32)$$

where $t_{ji}$ is $a_{ji}$ filtered by Hemming window $$t_{ji} = \sum_{m=1}^{M_j} h_{jm} d_{jim} \Delta l. \quad (33)$$

Both SVD and SART can be generalized to curved most probable diffusion paths. In priEdpie, the curved path is achieved through iterations using straight line segments. From the solution based on the straight most probable diffusion path described above, Equation (21), Equation (24), or Equation (28) can be used to find the curved most probable diffusion path, after which either single valued decomposition or simultaneous algebraic reconstruction techniques can be applied.

Another method for use with WKB near infrared image reconstruction, which is used in virtually all the modern computer tomography methodologies based on straight paths, is the filtered backprojection method. This methodology generates images that are far more accurate, and requires far less computational time. The drawback is that it cannot be generalized to curved most probable diffusion paths, because the Fourier slice theorem, on which the backprojection method is based, is valid only for straight line projections. The following are the basic ideas of incorporating the filtered backprojection method into the WKB imaging methodology.

Figure 18:
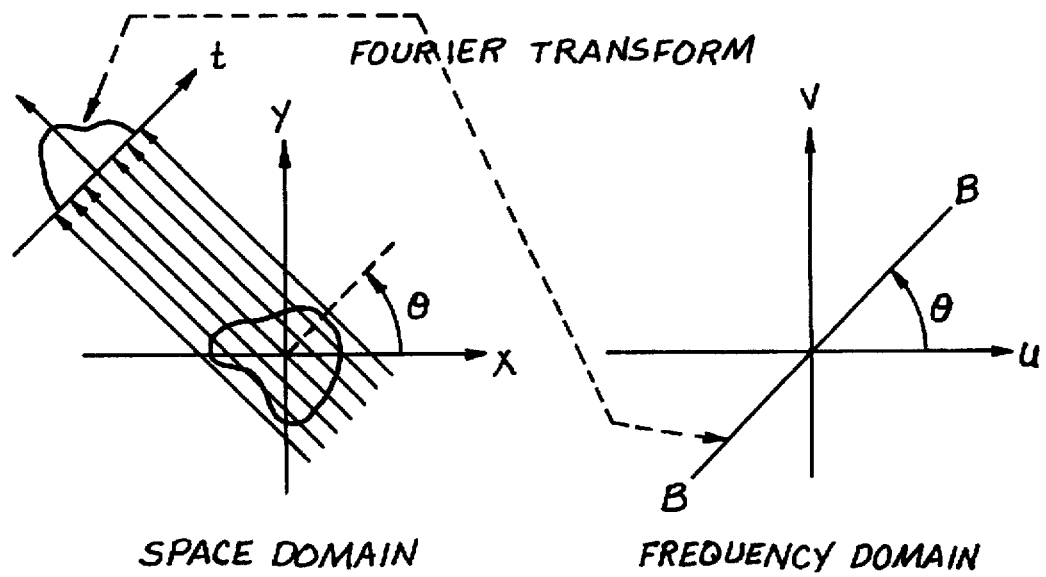
FIG. 18 is a diagram which illustrates the use of the Fourier Slice Theorem which relates the Fourier transform of a projection to the Fourier transform of the imaged object along a radial line.

To simplify the discussion, assume parallel beam projection (see FIG. 18). If the object is represented by a function $f(x,y)$ (corresponding to $\delta\mu_a(x)$ or $\kappa(x)$), then the projection at an angle $\theta$ is $$P_\theta(t) = \int_{(\theta,t)\text{line}} f(x,y) dl, \quad (34)$$

where dl is along the projection path and $t = x \cos \theta + y \sin \theta$.

The method here is based on the Fourier slice theorem, which relates the Fourier transform of $P_\theta(t)$ to the Fourier transform of $f(x,y)$ along the $\theta$ direction (line $\overline{BB}$) in FIG. 18. This is easily seen, since (t,l) forms an orthogonal coordinate system and the Jacobian with respect to (x,y) is unity. Thus $$P_\theta(w) = \int P_\theta(t) e^{j2\pi wt} dt = \int\int f(x,y) e^{j2\pi wt} dt dl \quad (35)$$
$$= \int\int f(x,y) e^{j2\pi(w\cos\theta x + w\sin\theta y)} dx dy =$$
$$F(w\cos\theta, w\sin\theta)$$

where $F(u,v)$ is the Fourier transform of $f(x,y)$. Therefore, if projections at all angles are known, one can obtain $F(u,v)$, and the inverse Fourier transform allows the recovery of $f(x,y)$. In practice, one can only obtain projections at a finite number of angles and additional procedures are necessary to reduce noise. First, one needs to use polar coordinates $$f(x,y) = \int\int F(u,v) e^{-j2\pi(ux+vy)} du dv = \int_0^{2\pi} \int_{-\infty}^{\infty} F(w,\theta) e^{-j2\pi w(\cos\theta x + \sin\theta y)} w \, dw \, d\theta \quad (36)$$
$$= \int_0^{2\pi} \left[ \int_{-\infty}^{\infty} P_\theta(w) e^{-j2\pi wt} w \, dw \right] d\theta \equiv \int_0^{2\pi} Q_\theta(t) d\theta$$

where $Q_\theta(t)$ can be thought of as the filtered projection (by $\omega$), which can also be written $$Q_\theta(t) = \int P_\theta(\tau) p(t-\tau) d\tau, \quad (37)$$

where $p(\tau)$ is the inverse Fourier transform of $\omega$ (more specifically $\omega \exp(-e|\omega|)$).

There are a few more steps involved in order to improve the image quality during the actual computer implementation of the filtered backprojection method. If W is the highest frequency (the inverse of the sampling interval in t space), then instead of $\omega$ in Equation (36), one can introduce a Hemming window and $$Q_\theta(t) = \int_{-\infty}^{\infty} P_\theta(w) e^{-j2\pi wt} g(w) H(w) dw, \quad (38)$$

where $H(\omega)$ is a smoothing function and $$g(w) = \begin{cases} w, & \text{when } w < |W|, \\ 0, & \text{otherwise.} \end{cases}$$

More efficient results are also obtained by zero-padding $P_\theta(t)$, i.e., by supplementing zeros to both sides of the function to increase its value range. This method can also be applied to the fan beam projections from a point light source.

Because of the high quality and speed of the filtered backprojection image reconstruction method, it should be used to construct the first order image. The final version of the WKB imaging software package will probably combine the filtered backprojection method for the first order image and the SART method for improving the resolution with curved most probable diffusion paths.

Extending the WKB image reconstruction methodology to the third-dimension is straight forward. One can first divide the 3D imaging volume into slices and construct 2D images for each slice. Again, the first order image can be reconstructed by using the filtered backprojection technique. However, this slice-by-slice procedure cannot be used if the curved most probable diffusion path is included to improve the image resolution because the curved most probable diffusion path can exit a slice's plane where the most probable diffusion path starts. Therefore, the inclusion of curved most probable diffusion paths in 3D requires the immediate construction of the 3D image at once. This might lead to a more stringent computer memory requirement. However, since one already has the first order image, one can concentrate on the volume part of interest and therefore solve a set of linear equations of much smaller size.

Near infrared imaging methodology has clear advantages over existing imaging techniques, such as X-ray CT, MRI's and PET Scans. In terms of cost, near infrared imaging equipment is significantly less expensive to produce and operate than any of these existing imaging systems. For example, in the case of a near infrared brain scanner, the hardware system of FIG. 3 only requires an array of solid state laser diodes and a set of photomultiplier tubes, a multi-channel electronic radio-frequency (RF) modulator, a phase sensitive RF detection amplification system and a microcomputer for processing data generated in displaying the image on monitor 22.

From a clinical perspective, the near infrared imaging system at doses of less than 50 milliwatts produces no adverse effect on human tissues unlike X-rays upon which current CT systems are based. Additionally, the near infrared imaging system, when integrated with newly developed imaging software, combines the near infrared scanners advantage of easy portability and sturdiness with the WKB imaging method's extremely rapid computation. For situations where instantaneous feedback is critical, such as on battle fields or accident sites, the near infrared brain hematoma scanner can be taken directly to the field to the patient, making the system ideal for hematoma detection in trauma victims. As a near infrared breast scanner, the methodology is useful in eliminating some of the false positives that current mammography techniques produce which result in unnecessary and expensive biopsies.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, although certain classes of detectors, light sources, data and signal processing circuitry has been described, any system which is capable of providing near infrared light exposure and detection from which photon diffusion data can be measured and then signal processed according to the invention can be substituted without departing from the scope of the invention. Further, still although near infrared radiation has been described in the context of tissue tomography, images of other types of targets at other radiation frequencies can also be performed as long as the diffusion equation approximately describes the photon migration process in the target.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

APPENDIX

```
c SVD program for WKB near infrared image reconstruction
//IMF2LINA JOB TIME=(35,5)
//*SCHEDULE PRIORITY=1.5
//        EXEC    FORTCLG,LEVEL=N,RG=350M,
//
OPTIONS='OPT(3),VECTOR(REPORT),DC(LT1,LT2,LT3,LT4,LT5,LT6,LT
7)'
c
c  this code is for imaging of tumor by using Chance's
experimental data
c
        implicit double precision(a-h,o-z)
        PARAMETER(AMUA=0.008 ,D=0.331,CN=3.E11/1.33)
        PARAMETER(NX=40 ,NY=40
,XL=140.,YL=XL,DELTAX=XL/NX,DELTAY=YL/NY)
        parameter(n=nx*ny,     sstep=1.0,dstep=1.,iomega=1
)
        parameter(iom1=1 ,iom2=1
,ra=xl/2.,is0=128,id0=64,isd0=is0*id0)
        parameter(m=is0*id0,scale=10.) ! scale is for
compress overfllow
        parameter(m1=m*(iom2-iom1+1), naux=2*n+m1,iread=0)
c       real*8 u0(m1,n)
        real*8 mua(n),u(m1,n),        s(n),sj(n),aux0(naux)
          real*8 trans(m1,n)          !for coefficient
matrix
        integer  order1(n),order2(n),iout(n)
        real*8 tmp1(n),tmp2(n),xr(m1),xi(m1)
        real*8 omega(iomega),omegac(iomega),ymk(iomega)
        real*8 ak1(iomega),ak2(iomega),ampk(iomega)
         real ampt(iomega,is0,id0),bts(is0),bta(id0)
        real*8 rsid1(m1),rsid2(m1),rsid3(m1),rsid4(m1)
        real*8 ampl(m1 ),phasel(m1 ) ! for theory amp and
phase
        real   sourcex(is0),sourcey(is0) ! source
coordinates
        real detectx(is0,id0),detecty(is0,id0)! detector
coornidates
        real dissd(isd0)            !distance of sources
and detectors
        real tgalpha(isd0)          ! tangent for lines
        real yb(isd0),infin         !
y=kx+b,k=tg(alpha), yb=b
        real*8 xaxesx(isd0,0:150),xaxesy(isd0,0:150)
        real*8 yaxesx(isd0,0:150),yaxesy(isd0,0:150)
        real*8 work1(200),work2(200),workx(200),worky(200)
        integer numx(isd0),numy(isd0)
      PARAMETER(N1= 871,NAUX1=2*N1+M1)
        real*8 u1(m1,n1),s1(n1),aux1(naux1)
        real*8 root1(n),root2(n),root3(n1),root4(n)
        integer order3(n),order4(n)
c
        parameter(n2=  1,naux2=2*n2+m1)
```

```
              real*8 u2(ml,n2),s2(n2),aux2(naux2)
c
       parameter(n3=1   ,naux3=2*n3+ml)
              real*8 u3(ml,n3),s3(n3),aux3(naux3)
c
       parameter(n4=1   ,naux4=2*n4+ml)
              real*8 u4(ml,n4),s4(n4),aux4(naux4)
c
              complex*16 kappa(n)              ! for unknowns
              complex*16 right(m),ci           ! for right side
              COMPLEX*16 PHIO,PHIK,       AKI ! HOMOGENEOUS AND
SCALE
              real*8 root5(n),root6(n2),root7(n)
              parameter(ng=3)
              real*8
xg(2,ng),bg(2),gg(3),ee(ng),b0g(2),hg(3),ag(2,3)
              real*8 a0g(2,3)
              parameter(ldfjac=41,mk=41,nk=2)
              real*8
fjac(ldfjac,nk),fscale(mk),fvec(mk),rparam(7),
     &       md(nk),xguess(nk),xscale(nk)
              integer iparam(6)
              external fcn
              logical nolinear
              data nolinear/.false./
              DATA OMEGA/200./
              common/arg/omegac,ymk
c             common/orderl/workx,worky
              common/lt1/trans
              common/lt2/u
              common/lt3/ul,xaxesx,xaxesy
              common/lt4/u2,yaxesx,yaxesy
              common/lt5/u3
c             common/lt6/v
c             common/worksp/rwksp
c             real*8 rwksp(600000)
c             call iwkin(600000)
c
c
              call xuflow(0)
              pi=3.1415926
              ci=(0.d0,1.d0)
              infin=1.e12
9             format(e12.5)
21            format(e13.6,1x,f11.6)
c
              DO K=1,IOMEGA
               P1=2.*PI*OMEGA(K)*1.E6/(AMUA*CN)
               D1=P1**2
               P2=SQRT(1.+D1 ) + 1.
               AK1(K)=SQRT( AMUA/(2.*D)*P2 )
               AK2(K)=0.5 * AK1(K)/( AMUA*SQRT(1.+D1) )
               WRITE(*,*)'K=',K,' AK1=',AK1(K),' AK2=',AK2(K)
              ENDDO
```

2

```
c
c       read theory data  and computes coordinates of sources
and detector
c
        l=0
c       do k=iom1,iom2
        WRITE(*,*)'FRECQUENCY(MHZ)=',OMEGA(K)
        do is=1,is0
         read(22,31)bts(is),sourcex(is),sourcey(is)
         read(22,*)
         read(23,31)waste1,waste2,waste3
         read(23,*)
31       format(4x,3(e12.5,1x))
32       format('bts=',3(e12.5,1x))
c        write(*,32)bts(is),sourcex(is),sourcey(is)
c        do iw=1,66*1
c           read(22,*)
c           read(23,*)
c        enddo
         do id=1,id0
          read(22,10)bta(id),detectx(is,id),detecty(is,id),
     &    ampt0     ,phi01
          read(23,10)waste1, waste2,          waste3,
     &    amptk     ,phik1
          l=l+1
c         rsid1(l)=-log(ampt(k,is,id))
          rsid1(l)=    (amptk/ampt0)
c         write(*,10)bta(id),rsid1(l)
c         write(*,10)bta(id),detectx(is,id),detecty(is,id)
         enddo ! id
c        do iw=1,66*2
c           read(22,*)
c           read(23,*)
c        enddo
        enddo ! is
c       enddo ! k
c       write(*,*)' -LN(rights)   '
        do iw=1,l
c        if(rsid1(iw).gt.1.d0) then
c           rsid1(iw)=(rsid1(iw+1)+rsid1(iw-1))/2
c        endif
         pr=rsid1(iw)
         rsid1(iw)=-log(pr)*scale
c        write(*,*)'l=',iw,pr,rsid1(iw)
        enddo
c       if(k.ne.0) stop
c
c       write(*,*)' &&&  distance of sources and detectors
&&&'
c
c       l=0
c       do k=iom1,iom2
        lm=0
        do is=1,is0
```

```
              sx=sourcex(is)
              sy=sourcey(is)
              do id=1,id0
c                if(bts(is).eq.bta(id)) goto 901
                 dx=detectx(is,id)
                 dy=detecty(is,id)
c                l=l+1
c                rsidl(l)=-log(ampt(k,is,id))
c                if(k.eq.1) then
                 lm=lm+1
                 dissd(lm)=sqrt((sx-dx)2+(sy-dy)2)
                 if(abs(dx-sx).le.0.01) then
                 tgalpha(lm)=infin
                 else
                 tgalpha(lm)=(sy-dy)/(sx-dx)
                 endif
                 yb(lm)=sy-tgalpha(lm)*sx
c
write(*,11)is,id,l,lm,sx,sy,dx,dy,dissd(lm),tgalpha(lm),yb(l
m)
c                endif
901           enddo         ! id
            enddo           ! is
            write(*,*)'      l,lm=',l,lm
c         enddo             ! k
c         if(l.ne.0) stop
c
c         coefficient matrix to fill intial zeros
c
          do i=1,ml
            do j=1,n
              trans(i,j)=0.
            enddo
          enddo
c
c
          n0=0
          do i=1,nx
            do j=1,ny
              n0=n0+1
              iout(n0)=-1
            enddo
          enddo
c
c
c         coordinates of straight lines and subsquare boundaries
c
c         l=0
c         do k=iom1,iom2
          lm=0
          do is=1,is0
            sx=sourcex(is)
            sy=sourcey(is)
```

```
            do id=1,id0
c         if(bts(is).eq.bta(id)) goto 902
          dx=detectx(is,id)
          dy=detecty(is,id)
c         l=l+1
          lm=lm+1
          if(abs(dx-sx).le.0.001) then
          tgalpha(lm)=infin
          else
          tgalpha(lm)=(sy-dy)/(sx-dx)
          endif
          yb(lm)=sy-tgalpha(lm)*sx
            idx=int(dx/deltax)+1
            isx=int(sx/deltax)+1
            idy=int(dy/deltay)+1
            isy=int(sy/deltay)+1
c
          if( dx.lt. sx) then         !  dx<sx
          ij=0
          xaxesx(lm,ij)=dx
          xaxesy(lm,ij)=dy
          idx0=idx
          if(abs(idx*deltax-dx).lt.0.001)idx0=idx+1
          do ix=idx0 ,isx-1    ! ? # 1
            x1=ix*deltax
c           if(abs(tgalpha(lm)).le.infin           ) then
! @@@
                y1=tgalpha(lm)*x1+yb(lm)
                ij=ij+1
                xaxesx(lm,ij)=x1
                xaxesy(lm,ij)=y1
          enddo ! ix
          if(xaxesx(lm,ij).lt.sx) then
            ij=ij+1
          xaxesx(lm,ij)=sx
          xaxesy(lm,ij)=sy
          endif
          endif  !  dx<sx
c
          if( dx.gt.sx) then         !  dx>sx
          ij=0
          xaxesx(lm,ij)=dx
          xaxesy(lm,ij)=dy
            idx0=idx-1       ! ? now
c           if(idx.eq.nx)idx0=idx-2
            if(abs((idx-1)*deltax-dx).lt.0.0001) idx0=idx-2
          do ix=idx0 ,isx-0,-1   !  1 -- > 0
            x1=ix*deltax
c           if(abs(tgalpha(lm)).le.infin.and.dy.ne.sy) then
! @@@
                y1=tgalpha(lm)*x1+yb(lm)

ij=ij+1
                xaxesx(lm,ij)=x1
```

```
            xaxesy(lm,ij)=yl
         enddo ! ix
         if(xaxesx(lm,ij).ne.sx) then
           ij=ij+1
           xaxesx(lm,ij)=sx
           xaxesy(lm,ij)=sy
         endif
        endif !  dx> sx
        if(abs(dx-sx).le..001) then    ! dx=sx
           ij=0
           xaxesx(lm,ij)=dx
           xaxesy(lm,ij)=dy
           if(dy.lt.sy) then
             do iy=idy,isy-1
               yl=iy*deltay
               ij=ij+1
               xaxesx(lm,ij)=dx
               xaxesy(lm,ij)=yl
c
write(*,*)'dx=sx,iy,ij,yl,dx#1=',iy,ij,yl,dx
             enddo  ! iy
           endif
c
           if(dy.gt.sy) then
             idy0=idy-1
             if(idy0.eq.ny) idy0=idy-2
             do iy=idy0 ,isy,-1        ! ? # 3
               yl=iy*deltay
               ij=ij+1
               xaxesx(lm,ij)=dx
               xaxesy(lm,ij)=yl
c            write(*,*)'dx=sx,dy,sy=',   dx,sx,dy,sy
             enddo
           endif
           if(xaxesy(lm,ij).gt.sy) then
             ij=ij+1
             xaxesx(lm,ij)=sx
             xaxesy(lm,ij)=sy
           endif
         endif  !  sx=dx
c
         numx(lm)=ij
c        write(*,*)'is,id=',is,id
c        write(*,*)'dx.dy,sx,sy#x= ',dx,dy,sx,sy
         do i=0,ij
c          write(*,*)lm,i,xaxesx(lm,i),xaxesy(lm,i)
         enddo
c
         if(dy.lt.sy) then
           ij=0
           yaxesx(lm,ij)=dx
           yaxesy(lm,ij)=dy
           do iy=idy+0,isy-1   ! # 4
             yl=iy*deltay
```

```
c              if(abs(tgalpha(lm)).gt.0.01              x)
then   ! %%%
               xl=(yl-yb(lm))/tgalpha(lm)
               ij=ij+1
               yaxesx(lm,ij)=xl
               yaxesy(lm,ij)=yl
             enddo ! iy
           if(yaxesy(lm,ij).lt.sy)  then
             ij=ij+1
             yaxesx(lm,ij)=sx
             yaxesy(lm,ij)=sy
           endif
         endif   ! dy<sy
c
         if(dy.gt.sy) then
           ij=0
           yaxesx(lm,ij)=dx
           yaxesy(lm,ij)=dy
           idy0=idy-1
           if(idy0.eq.ny)idy0=idy-2
           do iy=idy0 ,isy+0,-1
             yl=iy*deltay
c              if(abs(tgalpha(lm)).gt.0.01              )
then   ! %%%
               xl=(yl-yb(lm))/tgalpha(lm)
               ij=ij+1
               yaxesx(lm,ij)=xl
               yaxesy(lm,ij)=yl
c            endif
           enddo ! iy
         if(yaxesy(lm,ij).gt.sy) then
         ij=ij+1
         yaxesx(lm,ij)=sx
         yaxesy(lm,ij)=sy
         endif
         endif ! dy>sy if(abs(dy-sy).lt.0.001) then    !  dy=sy
           ij=0
           yaxesx(lm,ij)=dx
           yaxesy(lm,ij)=dy
             if(dx.lt.sx) then
               do ix=idx,isx-1   ! dx<sx
                 xl=ix*deltax
                 ij=ij+1
                 yaxesx(lm,ij)=xl
                 yaxesy(lm,ij)=dy
               enddo   ! ix
             else
             do ix=idx-1,isx   ,-1
               xl=ix*deltax
               ij=ij+1
               yaxesx(lm,ij)=xl
               yaxesy(lm,ij)=dy
```

```
                        enddo   ! ix
                    endif       ! dx<sx
                    if(yaxesx(lm,ij).lt.sx) then
                      ij=ij+1
                      yaxesx(lm,ij)=sx
                      yaxesy(lm,ij)=sy
                    endif
                  endif   ! dy=sy
                  numy(lm)=ij
c
c             write(*,*)'dx.dy,sx,sy#y= ',dx,dy,sx,sy
              do i=0,ij
c               write(*,*)lm,i ,yaxesx(lm,i),yaxesy(lm,i)
              enddo
c
write(*,*)'lm,numx(lm),numy(lm)=',lm,numx(lm),numy(lm)
c
902         enddo       ! id
          enddo         ! is
          write(*,*)'l,lm=',l,lm
c         enddo         ! k
c
          lm0=lm
          l=0
          do k=iom1,iom2
            do lm=1,lm0
            if(lm.gt.lm0)                          then
            i0=numx(lm)
            write(*,*)'lm,i0 in data x =',lm,i0
            do i=0,i0
            write(*,10) xaxesx(lm,i),xaxesy(lm,i),tgalpha(lm)
            enddo i0=numy(lm)
            write(*,*)'lm,i0 in data y =',lm,i0
            do i=0,i0
            write(*,10)yaxesx(lm,i),yaxesy(lm,i)
            enddo
            endif j0=0
              do i=0,numx(lm)
                j0=j0+1
                workx(j0)=xaxesx(lm,i)
                worky(j0)=xaxesy(lm,i)
              enddo
              do i=0,numy(lm)
                j0=j0+1
                workx(j0)=yaxesx(lm,i)
                worky(j0)=yaxesy(lm,i)
              enddo
c
            x0=xaxesx(lm,0)
```

```
              xn=xaxesx(lm,numx(lm))
              y0=xaxesy(lm,0)
              yn=xaxesy(lm,numx(lm))
c
              if(x0.le.xn) then
                call downup(j0,workx,work1)
                if(y0.le.yn) call downup(j0,worky,work2)
                if(y0.gt.yn) call updown(j0,worky,work2)
c               do i=1,j0
c                 xaxesx(lm,i)=work1(i)
c                 xaxesy(lm,i)=work2(i)
c               enddo
              endif
              if(x0.gt.xn) then
                call updown(j0,workx,work1)
                if(y0.le.yn) call downup(j0,worky,work2)
                if(y0.gt.yn) call updown(j0,worky,work2)
c               do i=1,j0
c                 xaxesx(lm,i)=work1(i)
c                 xaxesy(lm,i)=work2(i)
c               enddo
c           write(*,*)'     x              y'
c             do i=1,j0
c               write(*,10)work1(i),work2(i)
c             enddo
              endif
c
              call cutsame(j0,work1,work2,workx,worky,j00)
              j0=j00
c
              if(lm.gt.lm0)              then
              write(*,*)'     x            y lm=',lm
                do i=1,j0
                  write(*,10)workx(i),worky(i),tgalpha(lm)
                enddo
              endif
c
c             l=0
c             do k=iom1,iom2
c               l=(k-1)*lm0+lm
                do i=1,j0-1
                  kx=int((workx(i))/deltax)+1
                  if(workx(i).gt.workx(i+1))
     $            kx=int((workx(i+1)+0.0001)/deltax)
                  if(worky(i).gt.worky(i+1))then
                    ky=int((worky(i+1))/deltay)
                  else
                    ky=int((worky(i))/deltay)
                  endif
c                 if(kx.eq.nx)kx=kx-1
                  if(ky.eq.ny)ky=ky-1
                  n0=ky*nx+kx
                  iout(n0)=0
                  ds=sqrt((workx(i )-workx(i +1))**2
```

```
     &                  +(worky(i )-worky(i +1))**2)
          if(n0.gt.n.or.n0.le.0)
write(*,*)'lm,kx,ky,n0,ds=',lm,kx,ky,n0,ds
          if(ds.le.0.d0.or.ds.gt.sqrt(2.)*deltax+0.0001)
     & write(*,*)'lm,i,n0,ds=',lm,i,n0,ds
c              if(ds.gt.sqrt(2.)*deltax) ds=sqrt(2.)*deltax
c              trans(lm,n0)=ds*ak2(k)*scale
               trans(lm,n0)=ds         *scale
c              trans(lm,n0)=ds
               if(n0.eq.n01)
     $         write(*,113)i,lm,n0,workx(i+0),kx,worky(i
),ky,ds
113
format(i3,1x,i4,1x,i4,1x,e12.5,1x,i3,1x,e12.5,1x,i3,1x,e12.5
)
c         if(trans(lm,n0).ne.0.)write(*,*)lm,n0,i,trans(lm,n0)
               n01=n0
             enddo
c          enddo   ! k
           enddo   ! lm
           enddo   ! k
c
c     if(i.ne.0) stop
c
c     signular value decomposition for a real matrix A
c
           do i=1,ml
             rsid2(i)=rsid1(i)
             rsid3(i)=rsid1(i)
             rsid4(i)=rsid1(i)
             do j=1,n
               u(i,j)=trans(i,j)
             enddo
           enddo
           call dgesvf(2,trans, ml,rsid1, ml,1,s ,  ml, n
,aux0,naux)
c          write(*,*)' whose weights are zeros?      '
           do i=1,n
             write(*,37)i,s(i)
           enddo
37         format('s(',i5,')=',e12.5)
c
c     solve unknown (Dela(Mua) =( V ). ( diag(1/sj) ) .( Ut
).( RIGHT )
c
           do j=1,n
             if(s(j).ge.5.d-2) then
c            if(s(j).ne.0.d0 ) then
             tmp1(j)=rsid1(j)/s(j)
             endif
           enddo
c
           do j=1,n
             sum=0.d0
```

```
              do jj=1,n
                sum=sum+trans(j,jj)*tmp1(jj)
              enddo
              root1(j)=sum
            enddo
c
              write(*,*) ' Delta(Mua)             '
              l=0
              do iy=1,ny
                do ix=1,nx
                  l=l+1
c                 if(
root1(l).lt.0.d0)root1(l)=0.d0
              write(*,10)iy*deltay,ix*deltax,root1(l)
            if(mod(l,nx).eq.0) write(*,*)'********',   1/nx ,
'**********'
              write(1,10)iy*deltay,ix*deltax,root1(l)
            if(mod(l,nx).eq.0) write(1,*)'********',   1/nx ,
'**********'
                enddo
              enddo
c
              j1=0
              do j=1,n
                root2(j)=root1(j)
                order1(j)=j
                order2(j)=j
                if(root1(j).gt.0.00000d0) then
                   j1=j1+1
                   order2(j )=0
                   do i=1,m1
                     u1(i,j1)=u(i,j)
                   enddo
                else
                   order1(j)=0
                  root1(j)=0.d0
                endif
              enddo
c
c          rmax=0.
c          do i=1,n
c            if(root1(i).gt.rmax) rmax=root1(i)
c          enddo
c          do i=1,n
c            root1(i)=root1(i)/rmax
c          enddo write(1,*)'j1=n1=',j1,'
order1,order2,root2,root1'
              write(2,*)'n1=',j1
              write(*,*)'n1=',j1
              do i=1,n
                if(root1(i).le..50e-3 .and.iout(i).eq.0)
root1(i)=.1 e-4
```

```
            if(iout(i).lt.0)root1(i)=-1.e-04
          enddo
                n0=0
                do i=1,nx
                   x=i*deltax
                   do j=1,ny
                      y=j*deltay
                      rr=sqrt((x-ra)**2+(y-ra)**2)
                      n0=n0+1
                      if(              rr.ge.ra-
10..and.iout(n0).eq.0)
     &                  root1(n0)=.1e-4
                   enddo
                enddo
             do i=1,n
               write(2,10)root1(i)
write(1,111)order1(i),order2(i),root2(i),root1(i)
             if(mod(i,nx).eq.0) write(1,*)'********', i/nx ,
'**********'
             if(mod(i,nx).eq.0) write(2,*)'********', i/nx ,
'**********'
             enddo
c        IF(I.NE.0)STOP
c
         call dgesvf(2,  u1 , m1,rsid2, m1,1,s1 , m1,
n1,aux1,naux1)
         do j=1,n1
           if(s1(j).ge.1.d-2) then
           tmp1(j)=rsid2(j)/s1(j)
           endif
         enddo
c
         do j=1,n1
          sum=0.d0
          do jj=1,n1
          sum=sum+u1(j,jj)*tmp1(jj)
          enddo
          root3(j)=sum
         enddo
          write(1,*)' i,root3'
          do i=1,n1
             write(1,*)i,root3(i)
          enddo
c
         j2=0
         do j=1,n
          root4(j)=root1(j)
          if(order2(j).eq.0) then
            j2=j2+1
            root4(j)=root3(j2)
c         if(root4(j).le.0.00010d0) root4(j)=0.d0     !
Notes
          endif
```

```
            enddo
            write(*,*)'j2=n1=',j2,' order1,2; root2,1,4'
            write(1,*)'j2=n1=',j2,' order1,2; root2,1,4'
            write(2,*)'n1=',j2
            do i=1,n
                if(root4(i).le..50e-3 .and.iout(i).eq.0)
 root4(i)=.1 e-4
                if(iout(i).lt.0)root4(i)=-1.e-4
            enddo
                    n0=0
                    do i=1,nx
                      x=i*deltax
                      do j=1,ny
                        y=j*deltax
                        rr=sqrt((x-ra)**2+(y-ra)**2)
                        n0=n0+1
                        if(            rr.ge.ra-
 10..and.iout(n0).eq.0)
        &              root4(n0)=.1e-4
                      enddo
                    enddo
            do i=1,n
              write(2,10)root4(i)

write(1,111)order1(i),order2(i),root2(i),root1(i),root4(i)
            if(mod(i,nx).eq.0) write(2,*)'********',  i/nx ,
 '**********'
            if(mod(i,nx).eq.0) write(1,*)'********',  i/nx ,
 '**********'
            enddo
            if(i.ne.0)stop
c
c       end of the first circle
c       begin of the second circle
c
            j1=0
            do j=1,n
              root5(j)=root4(j)
              order3(j)=j
              order4(j)=j
              if(root4(j).gt.0.00001d0) then
                j1=j1+1
                order4(j )=0
                do i=1,m1
                  u2(i,j1)=u(i,j)
                enddo
              else
                order3(j)=0
                root4(j)=0.d0
              endif
            enddo
              write(1,*)'j2=n2=',j1,' order3,4; root5,4'
              write(2,*)'j2=n2=',j1
              do i=1,n
```

```
           write(1,111)order3(i),order4(i),root5(i),root4(i)
                   write(2,10)
root4(i)
           if(mod(i,nx).eq.0) write(1,*)'********',  i/nx ,
'**********'
           if(mod(i,nx).eq.0) write(2,*)'********',  i/nx ,
'**********'
            enddo
            if(i.ne.0)stop
c
           call dgesvf(2,  u2 , m1,rsid3, m1,1,s2 , m1,
n2,aux2,naux2)
         do j=1,n2
           if(s2(j).ge.1.d-4) then
           tmp1(j)=rsid3(j)/s2(j)
           endif
           enddo
c
         do j=1,n2
          sum=0.d0
          do jj=1,n2
           sum=sum+u2(j,jj)*tmp1(jj)
          enddo
          root6(j)=sum
         enddo
         write(1,*)'i, root6'
          do i=1,n2
             write(1,*)i,root6(i)
          enddo
c
         j2=0
         do j=1,n
           root7(j)=root4(j)
           if(order4(j).eq.0) then
              j2=j2+1
              root7(j)=root6(j2)
c             if(root7(j).lt.0.001d0) root7(j)=0.d0
c             if(j.lt.70)root7(j)=0.d0
c             if(j.gt.290)root7(j)=0.d0
           endif
          enddo
          write(1,*)'j2=n2',j2,' order3,4; root5,4,7'
          do i=1,n write(1,111)order3(i),order4(i),root5(i),root4(i),root7(i)
           if(mod(i,nx).eq.0) write(1,*)'********',  i/nx ,
'**********'
            enddo
c
c       end of the second circle
c       begin of the third circle
           do i=1,n
              root1(i)=root7(i)
```

```
          enddo
c
          j1=0
          do j=1,n
           root2(j)=root1(j)
           order1(j)=j
           order2(j)=j
           if(root1(j).gt.0.00001d0) then
             j1=j1+1
             order2(j )=0
             do i=1,m1
               u3(i,j1)=u(i,j)
             enddo
           else
             order1(j)=0
             root1(j)=0.d0
           endif
          enddo
          write(1,*)'j1=n3=',j1,'
 order1,order2,root2,root1'
          write(2,*)'j1=n3=',j1
          do i=1,n
           if(root1(i).le..10e-4 .and.iout(i).eq.0)
 root1(i)=.1 e-4
           if(iout(i).lt.0)root1(i)=-1.e-5
          enddo
          do i=1,n write(1,111)order1(i),order2(i),root2(i),root1(i)
           if(mod(i,nx).eq.0) write(1,*)'********', i/nx , '
 *******'
           write(2,10)
 root1(i)
           if(mod(i,nx).eq.0) write(2,*)'********', i/nx , '
 *******'
          enddo
          if(i.ne.0)stop
c
          call dgesvf(2, u3 , m1,rsid3, m1,1,s3 , m1,
 n3,aux3,naux3)
          do j=1,n3
           if(s3(j).ge.1.d-4) then
            tmp1(j)=rsid3(j)/s3(j)
           endif
          enddo
c
          do j=1,n3
           sum=0.d0
           do jj=1,n3
            sum=sum+u3(j,jj)*tmp1(jj)
           enddo
           root3(j)=sum
          enddo
          write(1,*)' i,root3'
```

```
            do i=1,n3
              write(1,*)i,root3(i)
            enddo
c
            j2=0
            do j=1,n
             root4(j)=root1(j)
             if(order2(j).eq.0) then
               j2=j2+1
               root4(j)=root3(j2)
c              if(root4(j).le.0.00001d0) root4(j)=0.d0
             endif
            enddo
            write(1,*)'j2=n3=',j2,' order1,2; root2,1,4'
             do i=1,n
write(1,111)order1(i),order2(i),root2(i),root1(i),root4(i)
          if(mod(i,nx).eq.0) write(1,*)'********',  i/nx ,
'**********'
             enddo
c
c       end of the third circle
c       begin of the fourth circle
c
             j1=0
             do j=1,n
              root5(j)=root4(j)
              order3(j)=j
              order4(j)=j
              if(root4(j).gt.0.00001d0) then
                j1=j1+1
                order4(j )=0
                do i=1,m1
                  u4(i,j1)=u(i,j)
                enddo
              else
                order3(j)=0
                root4(j)=0.d0
              endif
             enddo
             write(1,*)'j2=n4=',j1,' order3,4; root5,4'
             write(2,*)'j2=n4=',j1
             do i=1,n
write(1,111)order3(i),order4(i),root5(i),root4(i)
             write(2,10)
root4(i)
             if(mod(i,nx).eq.0) write(1,*)'********',  i/nx ,
'**********'
             if(mod(i,nx).eq.0) write(2,*)'********',  i/nx ,
'**********'
             enddo
c        if(i.ne.0)stop
c
```

```
              call dgesvf(2,  u4  , ml,rsid4, ml,1,s4  , ml,
n4,aux4,naux4)
         do j=1,n4
           if(s4(j).ge.1.d-4) then
           tmpl(j)=rsid4(j)/s4(j)
           endif
           enddo
c
         do j=1,n4
          sum=0.d0
          do jj=1,n4
           sum=sum+u4(j,jj)*tmpl(jj)
          enddo
          root6(j)=sum
         enddo
         write(1,*)'i, root6'
          do i=1,n4
             write(1,*)i,root6(i)
          enddo
c
         j2=0
         do j=1,n
           root7(j)=root4(j)
           if(order4(j).eq.0) then
              j2=j2+1
              root7(j)=root6(j2)
              if(root7(j).lt.0.0001d0) root7(j)=0.d0
c             if(j.lt.120)root7(j)=0.d0
c             if(j.gt.290)root7(j)=0.d0
           endif
         enddo
           write(1,*)'j2=n4=',j2,' order3,4; root5,4,7'
           write(2,*)'j2=n4=',j2
           do i=1,n
write(1,111)order3(i),order4(i),root5(i),root4(i),root7(i)
          if(mod(i,nx).eq.0) write(1,*)'********',   i/nx ,
'**********'
           write(2,10)
root7(i)
          if(mod(i,nx).eq.0) write(2,*)'********',   i/nx ,
'**********'
           enddo
c
c     end of the fourth circle
c
c
           if(i.ne.0)stop
              j3=0
              l=0
              do i=1,ny
                do j=1,nx
                 l=l+1
                 if(root7(l).le.0.d0)root7(l)=0.d0
```

```
                if(root7(1).gt.0.d0)j3=j3+1
                write(2,10)                        root7(1)
                write(1,10)i*deltay,j*deltax,root7(1)
                if(mod(1,nx).eq.0)write(1,*)'*********',1/nx,'
******!
                if(mod(2,nx).eq.0)write(1,*)'*********',1/nx,'
******!
              enddo
            enddo
            write(1,*)'nun zeros #=',j3
c
111     format(i4,1x,i4,e12.5,1x,e12.5,1x,e12.5)
11         format(4(i4,1x),4(f6.3,1x),3(e11.4,1x))
12        format('id=',i3,' xd=',e12.5,' yd=',e12.5)
14     format('m=',i3,' n=',i3, ' mua=      ',4e12.5)
10      format(6(e12.5,1x))
15       format(e12.6,f12.6)
         end
         subroutine downup(n,a,b)
         real*8 a(200)  ,b(200)
c        common/order1/a,b
         do i=1,n
         aw= 1.e70
            do j=1,n
              if(a(j).lt.aw) then
                aw=a(j)
                j0=j
              endif
            enddo
            b(i)=aw
            a(j0)= 1.e70
         enddo
         return
         end
c
c
c
         subroutine updown(n,a,b)
         real*8 a(200)  ,b(200)
c        common/order1/a,b
          do i=1,n
         aw=-1.e70
            do j=1,n
              if(a(j).gt.aw) then
                aw=a(j)
                j0=j
              endif
            enddo
            b(i)=aw
            a(j0)=-1.e70
          enddo
          return
          end
c
```

```
c
       subroutine cutsame(n,a,b,c,d,j)
       real*8 a(200),b(200),c(200),d(200)

c(1)=a(1)
       d(1)=b(1)
        j=2
        do i=2,n
          if(abs(a(i)-a(i-1)).lt.0.001.and.
     &        abs(b(i)-b(i-1)).lt.0.001) go to 10
          c(j)=a(i)
          d(j)=b(i)
          j=j+1
10      enddo
        j=j-1
        return
        end
c
//GO.FT01F001 DD DISP=(OLD,CATLG),DSN=IMF2LIN.ROOTS3,
//     UNIT=DATA,SPACE=(TRK,(100,100),RLSE)
//GO.FT02F001 DD DISP=(OLD,CATLG),DSN=IMF2LIN.ROOTS.DATA1,
//     UNIT=DATA,SPACE=(TRK,(100,100),RLSE)
c/GO.FT22F001 DD DISP=(OLD,CATLG),DSN=IMF2LIN.SPHT20,
c/GO.FT22F001 DD DSN=IMF2LIN.IMAGE.THEORY.W2000MHZ.D3MM,
c/     DISP=(OLD,CATLG),UNIT=DATA,SPACE=(TRK,(10,1),RLSE)
c/GO.FT22F001 DD DISP=(OLD,CATLG),DSN=IMF2LIN.DATA2K.SMALL,
c/GO.FT22F001 DD DISP=(OLD,CATLG),DSN=IMF2LIN.SPHT20.SMALL,
//GO.FT22F001 DD
DISP=(OLD,CATLG),DSN=IMF2LIN.BRAIN.F200MHZ.DATA0,
//     UNIT=DATA,SPACE=(TRK,(10,1),RLSE)
//GO.FT23F001 DD
DISP=(OLD,CATLG),DSN=IMF2LIN.BRAIN.F200MHZ.A5X2.DATA2,
//     UNIT=DATA,SPACE=(TRK,(10,1),RLSE)
```

```
c SART Program for WKB near infrared image reconstruction
//IMF2LIN3 JOB TIME=(06,9)
//*SCHEDULE PRIORITY=1.5
//         EXEC     FORTCLG,LEVEL=N,RG=1M,
//   OPTIONS='OPT(3),VECTOR(REPORT)'
c
c  this code is for imaging of tumor by using Chance's
experimental data
c
        implicit double precision(a-h,o-z)
        parameter(amua=0.003 ,d=0.208,cn=3.e11/1.33)
PARAMETER(NX=128,NY=128,XL=140.,YL=XL,DELTAX=XL/NX,DELTAY=YL
/NY)
        parameter(n=nx*ny,omega=200.)
        parameter(ra=xl/2.,is0=128,id0=64,isd0=is0*id0)
        parameter(scale= 10.)
        parameter(ml=is0*id0)
        real*8 dmua0(n),dmua1(n)
        real ak1,ak2
        real bts(is0),bta(id0),sumij(n),dm(n)
        real*8 rsidl(ml)
        real  sourcex(is0),sourcey(is0) !  source
coordinates
        real detectx(is0,id0),detecty(is0,id0)!  detector
coornidates
        real dissd(isd0)             !distance of sources
and detectors
        real tgalpha                 ! tangent for lines
        real yb,infin                ! y=kx+b,k=tg(alpha),
yb=b
        real xaxesx(0:500),xaxesy(0:500)
        real yaxesx(0:500),yaxesy(0:500)
        real*8 work1(500),work2(500),workx(500),worky(500)
        integer numx,numy,iout(n)
c
        call xuflow(0)
c
        pi=3.1415926
        infin=1.e12
9       format(e12.5)
21      format(e13.6,1x,f11.6)
c
        p1=2.*pi*omega*1.e6/(amua*cn)
        d1=p1**2
        p2=sqrt(1.+d1 ) + 1.
        ak1  =sqrt( amua/(2.*d)*p2 )
        ak2  =0.5 * ak1  /( amua*sqrt(1.+d1) )
        write(*,*)'ak1=',ak1   ,' ak2=',ak2
c
c       read theory data  and computes coordinates of sources
and detector
c
```

```
                l=0
                do is=1,is0
                  read(22,31)bts(is)
c                 if(k.eq.iom1) then
                  sourcex(is)=ra*cos(bts(is)          )+ra
                  sourcey(is)=ra*sin(bts(is)          )+ra
c                 write(*,*)sourcex(is),sourcey(is)
c                 endif
                  do id=1,id0
                    read(22,*)bta(id),ampt
                    l=l+1
                    rsid1(l)=-log(ampt)
                    detectx(is,id)=ra*cos(bta(id)         )+ra
                    detecty(is,id)=ra*sin(bta(id)         )+ra
c                   write(*,*)id,detectx(is,id),detecty(is,id)
                  enddo ! id
                enddo ! is
31      format(4x,g20.12)
c
c               write(*,*)' &&&   distance of sources and detectors
&&&'
c
c       l=0
c       do k=iom1,iom2
                lm=0
                do is=1,is0
                   sx=sourcex(is)
                   sy=sourcey(is)
                   do id=1,id0
c                     if(bts(is).eq.bta(id)) goto 901
                      dx=detectx(is,id)
                      dy=detecty(is,id)
                      lm=lm+1
                      dissd(lm)=sqrt((sx-dx)2+(sy-dy)2)
c                     if(abs(dx-sx).le.0.01) then
c                     tgalpha=infin
c                     else
c                     tgalpha=(sy-dy)/(sx-dx)
c                     endif
c                     yb=sy-tgalpha*sx
c
write(*,11)is,id,l,lm,sx,sy,dx,dy,dissd(lm),tgalpha,yb
c                     endif
901                enddo       ! id
                enddo          ! is
c               write(*,*)'    l,lm=',l,lm
c       enddo                  ! k
c
c
                do i=1,n
                  dmua0(i)=0.
                  dmua1(i)=0.
                  sumij(i)=0.
                  iout (i)=-1
```

```
              enddo
c
c    coordinates of straight lines and subsquare boundaries
c
c       l=0
c       do k=iom1,iom2
        itera=0
55555   itera=itera+1
        do i=1,n
          dm(i)=0.
        enddo
        lm=0
        do 22222 is=1,is0
          sx=sourcex(is)
          sy=sourcey(is)
          do 11111 id=1,id0
            dx=detectx(is,id)
            dy=detecty(is,id)
            lm=lm+1
            if(abs(dx-sx).le.0.001) then
              tgalpha=infin
            else
              tgalpha=(sy-dy)/(sx-dx)
            endif
            yb=sy-tgalpha*sx
              idx=int(dx/deltax)+1
              isx=int(sx/deltax)+1
              idy=int(dy/deltay)+1
              isy=int(sy/deltay)+1
c
              if( dx.lt. sx) then        !   dx<sx
              ij=0
              xaxesx(ij)=dx
              xaxesy(ij)=dy
              idx0=idx
              if(abs(idx*deltax-dx).lt.0.001)idx0=idx+1
              do ix=idx0 ,isx-1
               x1=ix*deltax
                  y1=tgalpha*x1+yb
                  ij=ij+1
                  xaxesx(ij)=x1
                  xaxesy(ij)=y1
              enddo ! ix
              if(xaxesx(ij).lt.sx) then
                 ij=ij+1
              xaxesx(ij)=sx
              xaxesy(ij)=sy
              endif   !  xaxesx(ij)<sx
              endif   !   dx<sx
c
              if( dx.gt.sx) then         !  dx>sx
              ij=0
              xaxesx(ij)=dx
              xaxesy(ij)=dy
```

```
              idx0=idx-1        ! ? now
 c            if(idx.eq.nx)idx0=idx-2
              if(abs((idx-1)*deltax-dx).lt.0.0001) idx0=idx-2
              do ix=idx0 ,isx-0,-1    !  1 -- > 0
               x1=ix*deltax
                  y1=tgalpha*x1+yb
                  ij=ij+1
                  xaxesx(ij)=x1
                  xaxesy(ij)=y1
              enddo ! ix
              if(xaxesx(ij).ne.sx) then
               ij=ij+1
              xaxesx(ij)=sx
              xaxesy(ij)=sy
              endif
             endif !  dx> sx
 c
             if(abs(dx-sx).le..001) then   ! dx=sx
                ij=0
                xaxesx(ij)=dx
                xaxesy(ij)=dy
                if(dy.lt.sy) then
                  do iy=idy,isy-1
                    y1=iy*deltay
                    ij=ij+1
                    xaxesx(ij)=dx
                    xaxesy(ij)=y1
 c
write(*,*)'dx=sx,iy,ij,y1,dx#1=',iy,ij,y1,dx
                  enddo ! iy
                endif   ! dy<sy
 c
                if(dy.gt.sy) then
                   idy0=idy-1
                   if(idy0.eq.ny) idy0=idy-2
                   do iy=idy0 ,isy,-1
                     y1=iy*deltay
                     ij=ij+1
                     xaxesx(ij)=dx
                     xaxesy(ij)=y1
 c                   write(*,*)'dx=sx,dy,sy=',  dx,sx,dy,sy
                   enddo
                endif    ! dy>sy
                if(xaxesy(ij).gt.sy) then
                  ij=ij+1
                  xaxesx(ij)=sx
                  xaxesy(ij)=sy
                endif
             endif  !  sx=dx
 c
              numx=ij
 c           write(*,*)'is,id=',is,id
 c           write(*,*)'dx.dy,sx,sy#x= ',dx,dy,sx,sy
 c           do i=0,ij
```

```
c            write(*,*)lm,i,xaxesx(i),xaxesy(i)
c          enddo
c
           if(dy.lt.sy) then        ! dy<sy
             ij=0
             yaxesx(ij)=dx
             yaxesy(ij)=dy
             do iy=idy+0,isy-1    ! # 4
              yl=iy*deltay
c             if(abs(tgalpha).gt.0.01              x) then
! %%%
                xl=(yl-yb)/tgalpha
                ij=ij+1
                yaxesx(ij)=xl
                yaxesy(ij)=yl
              enddo ! iy
             if(yaxesy(ij).lt.sy)   then
               ij=ij+1
               yaxesx(ij)=sx
               yaxesy(ij)=sy
             endif
           endif   ! dy<sy
c
           if(dy.gt.sy) then
             ij=0
             yaxesx(ij)=dx
             yaxesy(ij)=dy
             idy0=idy-1
             if(idy0.eq.ny)idy0=idy-2
             do iy=idy0 ,isy+0,-1
              yl=iy*deltay
c             if(abs(tgalpha).gt.0.01) then   ! %%%
                xl=(yl-yb)/tgalpha
                ij=ij+1
                yaxesx(ij)=xl
                yaxesy(ij)=yl
c             endif
             enddo ! iy
          if(yaxesy(ij).gt.sy) then
          ij=ij+1
          yaxesx(ij)=sx
          yaxesy(ij)=sy
          endif
          endif ! dy>sy if(abs(dy-sy).lt.0.001) then   ! dy=sy
              ij=0
              yaxesx(ij)=dx
              yaxesy(ij)=dy
              if(dx.lt.sx) then
                do ix=idx,isx-1   ! dx<sx
                 xl=ix*deltax
                 ij=ij+1
                 yaxesx(ij)=xl
```

```
                              yaxesy(ij)=dy
                           enddo   ! ix
                         else
                           do ix=idx-1,isx   ,-1
                             xl=ix*deltax
                             ij=ij+1
                             yaxesx(ij)=xl
                             yaxesy(ij)=dy
                           enddo   ! ix
                         endif   ! dx<sx
                         if(yaxesx(ij).lt.sx) then
                           ij=ij+1
                           yaxesx(ij)=sx
                           yaxesy(ij)=sy
                         endif
                       endif   ! dy=sy
                       numy=ij
c
c           write(*,*)'dx.dy,sx,sy#y= ',dx,dy,sx,sy
c           do i=0,ij
c             write(*,*)lm,i ,yaxesx(i),yaxesy(i)
c           enddo
c           write(*,*)'lm,numx,numy=',lm,numx,numy
c
c 11111    enddo       ! id
c 22222    enddo       ! is
c         write(*,*)'lm=',lm
c
c         lm0=lm
c         l=0
c         do k=iom1,iom2
c           do lm=1,lm0
c           if(lm.gt.lm0)then
c           i0=numx
c           write(*,*)'lm,i0 in data x =',lm,i0
c           do i=0,i0
c           write(*,10) xaxesx(i),xaxesy(i),tgalpha
c           enddo
c
c           i0=numy
c           write(*,*)'lm,i0 in data y =',lm,i0
c           do i=0,i0
c           write(*,10)yaxesx(i),yaxesy(i)
c           enddo
c           endif
c
c
          j0=0
          do i=0,numx
            j0=j0+1
            workx(j0)=xaxesx(i)
            worky(j0)=xaxesy(i)
          enddo
          do i=0,numy
```

```
            j0=j0+1
            workx(j0)=yaxesx(i)
            worky(j0)=yaxesy(i)
          enddo
c
          x0=xaxesx(0)
          xn=xaxesx(numx)
          y0=xaxesy(0)
          yn=xaxesy(numx)
c
          if(x0.le.xn) then
            call downup(j0,workx,work1)
            if(y0.le.yn) call downup(j0,worky,work2)
            if(y0.gt.yn) call updown(j0,worky,work2)
c           do i=1,j0
c             xaxesx(i)=work1(i)
c             xaxesy(i)=work2(i)
c           enddo
          endif
          if(x0.gt.xn) then
            call updown(j0,workx,work1)
            if(y0.le.yn) call downup(j0,worky,work2)
            if(y0.gt.yn) call updown(j0,worky,work2)
c           do i=1,j0
c             xaxesx(i)=work1(i)
c             xaxesy(i)=work2(i)
c           enddo
c         write(*,*)'   x              y'
c            do i=1,j0
c              write(*,10)work1(i),work2(i)
c           enddo
          endif
c
          call cutsame(j0,work1,work2,workx,worky,j00)
          j0=j00
c
c         if(lm.gt.lm0)           then
c         write(*,*)'   x         y lm=',lm
c            do i=1,j0
c              write(*,10)workx(i),worky(i),tgalpha
c            enddo
c         endif
c
c         l=0
c         do k=iom1,iom2
c           l=(k-1)*lm0+lm
          aig=0.
          do i=1,j0-1
            kx=int((workx(i))/deltax)+1
            if(workx(i).gt.workx(i+1))
     $      kx=int((workx(i+1)+.00001)/deltax)
            if(worky(i).gt.worky(i+1))then
              ky=int((worky(i+1))/deltay)
            else
```

```
                    ky=int((worky(i))/deltay)
                  endif
c             if(kx.eq.nx)kx=kx-1
              if(ky.eq.ny)ky=ky-1
              n0=ky*nx+kx
              iout(n0)=0
              ds=sqrt((workx(i )-workx(i +1))**2
     &             +(worky(i )-worky(i +1))**2)
              aig=aig+ds*dmua0(n0)
              if(itera.eq.1)   sumij(n0)=sumij(n0)+ds
         if(n0.gt.n.or.n0.le.0)
write(*,*)'lm,kx,ky,n0,ds=',lm,kx,ky,n0,ds
         if(ds.le.0.d0.or.ds.gt.sqrt(2.)*deltax+0.0001)
     & write(*,*)'lm,i,n0,ds=',lm,i,n0,ds
c             if(ds.gt.sqrt(2.)*deltax) ds=sqrt(2.)*deltax
c             trans(lm,n0)=ds*ak2(k)
c             trans(lm,n0)=ds
              if(n0.eq.n01)
     $        write(*,113)i,lm,n0,workx(i+0),kx,worky(i
),ky,ds
c        if(trans(lm,n0).ne.0.)write(*,*)lm,n0,i,trans(lm,n0)
              n01=n0
           enddo ! j0
c
           if(itera.eq.1) go to 11111
c
           do i=1,j0-1
              kx=int((workx(i))/deltax)+1
              if(workx(i).gt.workx(i+1))
     $        kx=int((workx(i+1)+.00001)/deltax)
              if(worky(i).gt.worky(i+1))then
                 ky=int((worky(i+1))/deltay)
              else
                 ky=int((worky(i))/deltay)
              endif
c             if(kx.eq.nx)kx=kx-1
              if(ky.eq.ny)ky=ky-1
              n0=ky*nx+kx
              ds=sqrt((workx(i )-workx(i +1))**2
     &             +(worky(i )-worky(i +1))**2)
              dm(n0)=dm(n0)+ds/dissd(lm)*(rsid1(lm)-
aig)/sumij(n0)
           enddo ! j0
c          enddo ! k
c          enddo ! lm
c          enddo ! k
11111   continue ! id
22222   continue ! is
        if(itera.eq.1) go to 55555
        dmaxmua=-1.e-40
        s1=0.
        s2=0.
        do i=1,n
           if(iout(i).eq.0) then
```

```
              dmual(i)=dmua0(i)+dm(i)
              s1=s1+dmual(i)
              s2=s2+abs(dm(i))
c             d1=abs(dm(i))/dmual(i)
c             if(d1.gt.dmaxmua) dmaxmua=d1
            endif
          enddo
          dmaxmua=s2/s1
          write(*,*)'itera #=',itera,' error=',dmaxmua
          if(dmaxmua.gt.0.0500) then
            do i=1,n
              dmua0(i)=dmual(i)
            enddo
            go to 55555
          endif
          write(*,*) ' pixel values            '
c         do i=1,n
c
if(dmual(i).lt.0.001.and.iout(i).eq.0)dmual(i)=0.1e-3
c         write(2,10)dmual(i)
c         IF(MOD(I,NX).EQ.0) WRITE(2,*)'********', I /NX ,
'*********'
c         enddo
          D1=-1.E-10
          n0=0
          do j=1,ny
            y=j*deltay
            do i=1,nx
              x=i*deltax
              n0=n0+1
              rcut=sqrt((x-ra)**2+(y-ra)**2)
              IF(RCUT.GE.RA-
15..AND.IOUT(N0).EQ.0)DMUA1(N0)=0.1E-3

IF(DMUA1(N0).LT.0.0005.AND.IOUT(N0).EQ.0)DMUA1(N0)=0.1E-3
              IF(DMUA1(N0).GT.D1)D1=DMUA1(N0)
              write(2,10)dmual(n0)
c             IF(MOD(N0,NX).EQ.0) WRITE(2,*)'***', N0/NX ,
'***'
            enddo
          enddo
          WRITE(*,*)'MAXKAPPA=',D1
111       format(i4,1x,i4,e12.5,1x,e12.5,1x,e12.5)
113
format(i3,1x,i4,1x,i4,1x,e12.5,1x,i3,1x,e12.5,1x,i3,1x,e12.5
)
11        format(4(i4,1x),4(f6.3,1x),3(e11.4,1x))
12        format('id=',i3,' xd=',e12.5,' yd=',e12.5)
14      format('m=',i3,' n=',i3, ' mua=      ',4e12.5)
10       format(6(e12.5,1x))
15       format(e12.6,f12.6)
         end
         subroutine downup(n,a,b)
         real*8 a(500) ,b(500)
```

```
c         common/order1/a,b
          do i=1,n
          aw= 1.e70
             do j=1,n
                if(a(j).lt.aw) then
                  aw=a(j)
                  j0=j
                endif
             enddo
             b(i)=aw
             a(j0)= 1.e70
           enddo
           return
           end
c
c
c
          subroutine updown(n,a,b)
          real*8 a(500)  ,b(500)
c         common/order1/a,b
          do i=1,n
          aw=-1.e70
             do j=1,n
                if(a(j).gt.aw) then
                  aw=a(j)
                  j0=j
                endif
             enddo
             b(i)=aw
             a(j0)=-1.e70
           enddo
           return
           end
c
c
          subroutine cutsame(n,a,b,c,d,j)
          real*8 a(500),b(500),c(500),d(500)

c(1)=a(1)
          d(1)=b(1)
           j=2
           do i=2,n
             if(abs(a(i)-a(i-1)).lt.0.001.and.
     &          abs(b(i)-b(i-1)).lt.0.001) go to 10
             c(j)=a(i)
             d(j)=b(i)
             j=j+1
10         enddo
           j=j-1
           return
           end
//GO.FT02F001 DD DISP=(OLD,CATLG),DSN=IMF2LIN.ROOTS.DATA3,
//     UNIT=DATA,SPACE=(TRK,(5000,100),RLSE)
```

```
//GO.FT22F001 DD
DISP=(OLD,CATLG),DSN=IMF2LIN.INFINITE.F1KHZ.DATA,
//      UNIT=DATA,SPACE=(TRK,(10,1),RLSE)
```

We claim:

1. A method for optical tomography of a target having a shape and dimension disposed in space comprising:

exposing a target with an amplitude modulated optical signal generated by a source at a source position next to said target;

detecting said amplitude modulated optical signal from said source at a detection position next to said target, said source and detection positions defining a line of most probable diffusion path being defined between said source and detection positions;

repeatedly exposing said target and detecting said amplitude modulated optical signal to define to a pluraltity of said lines of most probable diffusion paths;

storing a pixel lattice in a computer memory corresponding to said space in which said target is located, said pixel lattice corresponding to a plurality of pixel cells, said line of most probable diffusion path between said source and detection positions being disposed across said plurality of pixel cells to select a subplurality of said pixel cells of said lattice;

storing a plurality of reference signals $J_O$ in said computer memory corresponding to an expected amplitude modulated optical signal for each pair of source and detection positions in a reference homogeneous medium with the same said dimension and shape as said target of which the absorption and scattering coefficients are constant and are chosen to be at least approximately equal to the average values of absorption and scattering coefficients respectively of said target; and generating a plurality of contrast diffusive propagation constant signals, $\delta\kappa(x_i)$, each contrast diffusive propagation constant being assigned to one of said subplurality of said pixel cells in which said line of most probable diffusion path between said source and detection positions is disposed, said contrast diffusive propagation constant signal being equal in magnitude to a difference in diffusive propagation constant signals of said target at a spatial position corresponding to each of said selected pixel cells within said pixel lattice, said difference being the difference between said diffusive propagation constant signal of said target to be imaged and said diffusive propagation constant signal of said reference homogeneous medium, wherein said contrast diffusive propagation constant signals are related to the computed photon flux $J_O$ at said detection position for the said reference homogeneous medium and measured photon flux $J_M$ at said detection position for the said target to be imaged by $$\sum_i \delta\kappa(x_i)\Delta l_i = \ln[J_O(b,a,\omega)/J_M(b,a,\omega)], \quad (39)$$

where $\delta\kappa(x_i)=\kappa(x_i)-\kappa_0$ is the contrast diffusive propagation constant of said target at angular modulating frequency $\omega$ of said amplitude modulation of said optical signal, $l_i$ is the length segment of said most probable diffusion path, and $\kappa_0$ is the diffusive propagation constant of the said reference homogeneous medium, where the sum is taken on said line of most probable diffusion path which has as its lowest order approximation a straight line-of-sight extending between said source position and said detection position, and where i is an index for each pixel on said line of most probable diffusion path;

storing said plurality of contrast diffusion propagation constant signals in said pixel lattice in said computer memory, whereby an optical tomograph of said target represented in said lattice may be provided.

2. The method of claim 1 where said contrast diffusion propagation constant signal is substituted by $$\frac{\kappa_0^*}{2\sqrt{\mu_{ao}^2+\omega^2}}\delta\mu_a(x_i),$$

where $\omega$ is the modulating frequency of said amplitude modulated optical signal, where $\mu_{ao}$ is the optical absorption coefficient of the said reference homogeneous medium, where the said diffusive propagation constant for the said reference homogeneous medium $\kappa_0$ is defined in Equation (40) below.

$$\kappa(\omega) = \kappa'(\omega) - i\kappa''(\omega), \quad (40)$$

$$\kappa'(\omega) = \frac{1}{\sqrt{2D_0}}\left(\sqrt{\mu_{ao}^2+\omega^2}+\mu_{ao}\right)^{1/2},$$

$$\kappa''(\omega) = \frac{1}{\sqrt{2D_0}}\left(\sqrt{\mu_{ao}^2+\omega^2}-\mu_{ao}\right)^{1/2},$$

with $D_0$ being the diffusion coefficient of the said reference homogeneous medium, where $\kappa_0^*$ is the complex conjugate of the said diffusive propagation constant for the reference homogeneous medium, where $\delta\mu_a(x_i)$ is defined as the contrast optical absorption coefficient signal for said pixel cell, said contrast optical absorption coefficient signal being equal in magnitude to a difference in said optical absorption coefficient of said target at a spatial position corresponding to each of said selected pixel cells within said pixel lattice, said difference being the difference between said optical absorption coefficient signal of said target to be imaged and said optical absorption coefficient signal of said reference homogeneous medium.

3. The method of claim 1 where said contrast diffusion propagation constant signal is substituted by $$\frac{\kappa_0^*}{2\sqrt{\mu_{ao}^2+\omega^2}}\delta\mu_a(x)-\frac{\kappa_0}{2D_0}\delta D(x),$$

where $\omega$ is the modulating frequency of said amplitude modulated optical signal, where $\mu_{ao}$ is the optical absorption coefficient of the said reference homogeneous medium, with $D_0$ is the diffusion coefficient of the said reference homogeneous medium, where the said diffusive propagation constant for the said reference homogeneous medium $\kappa_0$ is defined in Equation (41) below.

$$\kappa(\omega) = \kappa'(\omega) - i\kappa''(\omega), \quad (41)$$

-continued $$\kappa'(\omega) = \frac{1}{\sqrt{2D_0}} \left( \sqrt{\mu_{a0}^2 + \omega^2} + \mu_{a0} \right)^{1/2},$$

$$\kappa''(\omega) = \frac{1}{\sqrt{2D_0}} \left( \sqrt{\mu_{a0}^2 + \omega^2} - \mu_{a0} \right)^{1/2},$$

with $\kappa_0$ being the said diffusive propagation constant for the reference homegeneous medium, where $\kappa_0^*$ is the complex conjugate of the said diffusive propagation constant for the reference homogeneous medium, where $\delta\mu_a(x_i)$ is defined as the contrast optical absorption coefficient signal for said pixel cell, said contrast optical absorption coefficient signal being equal in magnitude to a difference in said optical absorption coefficient of said target at a spatial position corresponding to each of said selected pixel cells within said pixel lattice, said difference being the difference between said optical absorption coefficient signal of said target to be imaged and said optical absorption coefficient signal of said reference homogeneous medium, where $\delta D(x_i)$ is defined as the contrast diffusion coefficient signal for said pixel cell, said contrast diffusion coefficient signal being equal in magnitude to a difference in said diffusion coefficient of said target at a spatial position corresponding to each of said selected pixel cells within said pixel lattice, said difference being the difference between said diffusion coefficient signal of said target to be imaged and said diffusion coefficient of said reference homogeneous medium.

4. The method of claim 1 further comprising generating a graphic image from said plurality of diffusive propagation constants stored in said computer memory.

5. The method of claim 1 wherein said source position and detection position is taken at a plurality of pairs of positions next to said target, wherein said target is exposed, wherein said modulated optical signal is detected, wherein said lattice is defined and wherein said plurality of contrast diffusive propagation constants is generated for said plurality of pairs of source and detection positions so that each of said pixel cells in said lattice is traversed by at least one said most probable diffusion path for a said pair of source and detector position for which photon flux is measured.

6. The method of claim 5 further comprising generating a graphic image from said plurality of diffusive propagation constants.

7. The method of claim 6 wherein said plurality of source and detection positions lie in a plane so that a two-dimensional graphic image is generated.

8. The method of claim 6 wherein said plurality of said source and detection positions are disposed on a three-dimensional surface which includes said target so that a three-dimensional graphic image is generated.

9. The method of claim 1 wherein generation of said plurality of said contrast diffusive propagation constants is generated by means of single value decomposition of a plurality of linear equations for said contrast diffusive propagation constants.

10. The method of claim 1 wherein generation of said plurality of contrast diffusive propagation constants is generated by means of simultaneous algebraic reconstruction of said contrast diffusive propagation constants.

11. The method of claim 1 wherein generation of said plurality of contrast diffusive propagation constants is generated by means of filtered backprojection of said contrast diffusive propagation constants.

12. The method of claim 1 wherein said optical signal is a modulated near infrared signal.

13. The method of claim 12 wherein the wavelength of said near infrared signal is in the range of 700 to 900 nanometers.

14. The method of claim 1 further comprising exposing said target to said light source at a plurality of amplitude modulated frequencies in sequence.

15. The method of claim 14 where detecting said optical signal at said plurality of detection positions is performed simultaneously for each of said plurality of detection positions.

16. The method of claim 1 wherein said target is exposed by a plurality of light sources in sequence, said plurality of light sources being positioned at a plurality of distinct source positions so that time sequence identifies which of said plurality of light sources is activated.

17. The method of claim 16 where detecting said optical signal at said plurality of detection positions is performed simultaneously for each of said plurality of detection positions.

18. The method of claim 17 further comprising exposing said target to said light source at a plurality of amplitude modulated frequencies in sequence.

19. A method of producing a near infrared tomograph of a tissue mass comprising the steps of:

irradiating said tissue mass with an amplitude modulated light from a near infrared light source;

detecting said near infrared light at a plurality of detection positions;

determining a line of most probable photon diffusion path between said near infrared light source and each of said detection positions;

using said detected amplitude modulated near infrared light signals to solve for contrast diffusive propagation constants along said line using an equation that relates detected photon flux to photon flux for a homogeneous reference medium; and constructing an optical image of said tissue mass by repeatedly performing the determination of a line of most probable photon diffusion and the corresponding solution for contrast diffusive propagation constants such that all imaged portions of the tissue mass are reached by a most probable photon diffusion path for said source and some detection position, whereby a near infrared tomograph is provided, this image construction process being denoted WKB image reconstruction.

20. The method of claim 19 further comprising the step of irradiating said tissue mass with amplitude modulated near infrared light from a plurality of near infared light sources, each of said sources defining a distinct line of most probable photon diffusion path for WKB image reconstruction with each of a plurality of near infrared detectors at each of said detection positions.

21. The method of claim 19 further comprising irradiating said tissue mass with amplitude modulated near infrared light from said light source at a plurality of modulated frequencies.

22. The method of claim 21 further comprising the step of irradiating said tissue mass with amplitude modulated near infared light from a plurality of near infrared light sources, each of said sources defining a distinct one of a plurality of lines of most probable photon diffusion paths between said source and detection positions for WKB image reconstruction with each of a plurality of near infrared detectors at each of said detection positions.

23. The method of claim 19 where irradiating said tissue mass is performed by irradiating with a pulsed light source.

24. The method of claim 23 where reconstructing said optical image is performed by Fourier transforming time dependent optical data signals corresponding to said detected near infrared light to generate multi-frequency inputs for said WKB image reconstruction.

* * * * *

UNITED STATES PATENT AND TRADEMARK OFFICE
CERTIFICATE OF CORRECTION

PATENT NO. : 5,694,938
DATED : Dec. 9, 1997
INVENTOR(S) : Feng et al.

It is certified that error appears in the above-identified patent and that said Letters Patent is hereby corrected as shown below:

On the page and in col. 1, line 2, " MIMAGING " should read -- IMAGING --.

Col. 1, lines 4-9, should be deleted and substitute with the text below:

-- This invention was made with Government support under Grant No.: HL48509, awarded by the National Institutes of Health; Grant No.: DE-AC03-88ER45378, awarded by the Department of Energy; Grant No.: N00014-92-J-4004, awarded by the Office of Naval Research. The Government has certain rights in this invention --

Signed and Sealed this

Fifteenth Day of June, 1999

Attest:

Q. TODD DICKINSON

*Attesting Officer*     Acting Commissioner of Patents and Trademarks